United States Patent
Peters et al.

(10) Patent No.: US 6,649,801 B2
(45) Date of Patent: Nov. 18, 2003

(54) ANIONIC BORATE LIGANDS AND ZWITTERIONIC COMPLEXES FORMED THEREFROM

(75) Inventors: Jonas C. Peters, Pasadena, CA (US); John C. Thomas, Pasadena, CA (US); Connie Lu, Pasadena, CA (US); Theodore A. Betley, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/112,679

(22) Filed: Mar. 28, 2002

(65) Prior Publication Data
US 2003/0050493 A1 Mar. 13, 2003

Related U.S. Application Data

(60) Provisional application No. 60/280,638, filed on Mar. 30, 2001.

(51) Int. Cl.$^7$ ................................................. C07F 5/02
(52) U.S. Cl. ............................................. 568/2; 568/1
(58) Field of Search ........................................ 568/1, 2

(56) References Cited

U.S. PATENT DOCUMENTS

| | | | | |
|---|---|---|---|---|
| 3,188,345 A | * | 6/1965 | Burg et al. ................. | 562/807 |
| 3,240,815 A | * | 3/1966 | Wagner et al. ................. | 528/6 |
| 3,839,392 A | * | 10/1974 | Follows ...................... | 524/117 |
| 5,264,602 A | * | 11/1993 | Juge et al. ................... | 556/402 |
| 6,225,487 B1 | * | 5/2001 | Guram ......................... | 556/18 |

OTHER PUBLICATIONS

CA:132:12400 Journal of the American Chemical Society by Peters et al 121(42) pp 9871–9872 1999.*
Journal of the American Chem. Society vol. 123, by Thomas et al pp 5100–5101 2001.*
Bosnich (1998), "Asymmetric Catalysis. A Comparative Study of the Mechanisms of Intramolecular Hydroacylation and Hydrosilation," *Acc. Chem. Res.* 31(10):667–674.
Butts et al. (1996), "Syntheses and Structures of Alkyl and Aryl Halide Complexes of the Type [(PiPr$_3$)$_2$PtH($\eta^1$–XR)]BAr$_f$ and Analogues with Et$_2$O, THF, and H$_2$ Ligands. Halide–to Metal π Bonding in Halocarbon Complexes," *J. Am. Chem. Soc.* 118(47):11831–11843.
Chauvin (2000), "Zwitterionic Organometallates," *Eur. J. Inorg. Chem.* 577–591.
Drent et al. (1996), "Palladium–Catalyzed Alternating Copolymerization of Alkenes and Carbon Monoxide," *Chem. Rev.* 96(2):663–681.
Karsch et al. (1985), "Funtional Trimethylphophine Derivatives. 21. (Phosphinomethyl)aluminum Compounds: Phosphinomethyl–Bridged Dimers and X–ray Structures of [Me$_2$AlCH$_2$PMe$_2$]$_2$ and [ClAl(CH$_2$PMe$_2$)$_2$]$_2$," *Organometallics* 4(2):231–238.
Lu et al. (2002), "Catalytic Copolymerization of CO and Ethylene with a Charge Neutral Palladium(II) Zwitterion," *J. Am. Chem. Soc.* 124(19):5272–5273.
Peters et al. (1998), "Activation of Aromatic C–H Bonds by (dmpe)Pt(Me)X (X=Me, O$_2$CCF$_3$, OTf) Systems," *Organometallics* 17(20):4493–4499.
Schlecht et al. (1997), "Trimethylplatinum Triflate: A Versatile Building Block in Coordination Chemistry," *Angew. Chem. Int. Ed. Engl.* 36(18):1994–1995.
Stahl et al. (1998), "Homogeneous Oxidation of Alkanes by Electrophilic Late Transition Metals," *Angew. Chem. Int. Edit.* 37:2181–2192.
Thomas et al. (2001), "Benzene C–H Activation at a Charge Neutral Zwitterionic Platinum(II) Complex," *J. Am. Chem. Soc.* 123(21):5100–5101.
Zhong et al. (2002), "C–H Bond Activation by Cationic Platinum(II) Complexes: Ligand Electronic and Steric Effects," *J. Am. Chem. Soc.* 124(7):1378–1399.

* cited by examiner

Primary Examiner—Jean F. Vollano
(74) Attorney, Agent, or Firm—Reed & Eberle LLP; Shelley P. Eberle

(57) ABSTRACT

This invention provides an anionic borate ligand, and its synthesis. Zwitterionic complexes formed by the ligand and a metal, and Group 9 and 10 metals in particular, are described. Uses of the complexes in stoichiometric and catalytic reaction chemistry are also provided.

13 Claims, No Drawings

ANIONIC BORATE LIGANDS AND ZWITTERIONIC COMPLEXES FORMED THEREFROM

CROSS REFERENCE TO RELATED APPLICATIONS

This application claims the benefit of U.S. Provisional Application Serial No. 60/280,638 filed on Mar. 30, 2001.

FIELD OF THE INVENTION

This invention relates to anionic borate ligands, and bis(phosphino) and bis(amino) borate ligands in particular. The invention further relates to zwitterionic complexes formed between anionic borate ligands and metals, such complexes finding utility in numerous stoichiometric and catalytic applications.

BACKGROUND OF THE INVENTION

Cationic, coordinatively unsaturated metal centers have played a critical role in the development of organometallic catalysis, and exhibit a wide range of both stoichiometric and catalytic transformations. Such species are frequently generated by methide abstraction with a strong Lewis acid, and they can also be generated by protonation with an acid whose conjugate base is noncoordinating or weakly coordinating.

These cationic metal centers are amongst the most widely studied systems in organometallic research. Industrially important polymerization reactions often undergo key intermediary steps at cationic metal centers. With respect to transformations important to organic synthesis, cationic late metal fragments enjoy widespread use in C—E bond forming processes, where E is C, N, O, S, Si, H, and so forth. Moreover, cationic metal centers are promising candidates for the ultimate goal of selective activation and functionalization of light hydrocarbon substrates.

However, in spite of the advances in the art, there continues to be a need for improved methods of mediating reaction chemistry. The present invention addresses those needs by a unique approach to the chemistry of cationic species whereby charge neutral zwitterions incorporating a partially insulated borate counter-anion are used to mediate reaction chemistry related to their discrete cationic relatives. A review of the use of zwitterions in organometallic chemistry is described in Chauvin et al., *Eur. J. Inorg. Chem.* 577 (2000). Aside from the advantage of eliminating the need for a cocatalyst, there are several significant reactivity differences between the zwitterionic complex of the invention and traditionally cationic systems due to (i) differences in their relative electrophilicities, (ii) differences in donor ligand lability, and (iii) reduced or completely eliminated ion-pairing effects in the zwitterionic systems by comparison to their cationic counterparts. Further, solvents that dissolve ionic compounds almost always have polar, hence coordinating functional groups that can attenuate their reactivity. In principle, the zwitterionic complex of the invention will provide access to the chemistry of cationic metal centers in relatively non-polar hydrocarbon media.

SUMMARY OF THE INVENTION

One aspect of the invention relates to compound having the formula:

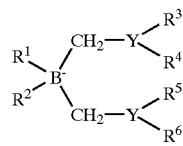

wherein: $R^1$ and $R^2$ are independently selected from the group consisting of alkyl and aryl; Y is selected from the group consisting of P and N; and $R^3$, $R^4$, $R^5$ and $R^6$ are independently selected from the group consisting of alkyl and aryl.

Another aspect of the invention pertains to a zwitterionic complex of the formula:

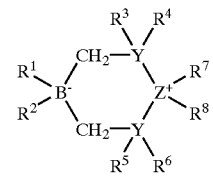

wherein: $R^1$ and $R^2$ are independently selected from the group consisting of alkyl and aryl; Y is selected from the group consisting of P and N; $R^3$, $R^4$, $R^5$ and $R^6$ are independently selected from the group consisting of alkyl and aryl; Z is a metal; and $R^7$ and $R^8$ are independently selected from the group consisting of halo, pseudo-halo, alkyl, aryl and mono or bidentate, displaceable neutral donor ligands.

Another aspect of the invention pertains to a zwitterionic complex of the formula III:

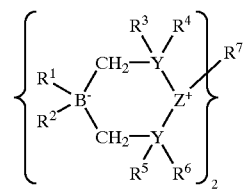

wherein: $R^1$ and $R^2$ are independently selected from the group consisting of alkyl and aryl; Y is selected from the group consisting of P and N; $R^3$, $R^4$, $R^5$ and $R^6$ are independently selected from the group consisting of alkyl and aryl; Z is a metal; and $R^7$ is selected from the group consisting of halo, pseudo-halo, alkyl, aryl and mono or bidentate, displaceable neutral donor ligands.

Yet another aspect of the invention relates to a method of catalyzing a reaction wherein transformation of a robust sigma bond in an organic compound is required, comprising: a) contacting the organic compound with i) an organic or inorganic reagent, and ii) a zwifferionic complex of an anionic borate ligand having the formula:

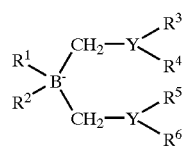

and a metal compound; wherein: $R^1$ and $R^2$ are independently selected from the group consisting of alkyl and aryl; Y is selected from the group consisting of P and N; and $R^3$, $R^4$, $R^5$ and $R^6$ are independently selected from the group consisting of alkyl and aryl; and b) producing an organic compound having a transformed robust sigma bond.

DETAILED DESCRIPTION OF THE INVENTION

The present invention relates to anionic borate ligands, and bis(phosphino) and bis(amino) borate ligands in particular. These negatively charged ligands can be installed on a variety of metals centers, and Group 9 and 10 metals in particular, and are especially useful for the preparation of neutral zwitterionic complexes. These zwitterionic complexes find utility in numerous applications in stoichiometric and catalytic reaction chemistry reminiscent of their discrete salt or ion-paired relatives. Examples of such applications include, by way of illustration and not limitation, benzene C—H activation processes (using platinum as the metal); catalytic hydroaminations (using palladium as the metal); polymerizations such as the copolymerization of ethylene and carbon monoxide (using palladium as the metal); organic transformations; polymerizations; alkane activation and functionalization reactions such as in alkane oxidation; as well as hydrogenation, hydrosilation, and hydroboration (all using rhodium as the metal).

The primary complex studied was a neutral platinum(II) alkyl complex supported by the anionic bidentate phosphine ligand $[Ph_2B(CH_2PPh_2)_2]$. A lithium adduct of an anionic, bis(phosphino)aluminate species is described in Karsch et al., *Organometallics* 4:231–238 (1985). The platinum system was examined for several reasons. First, C—H activation at Pt(II) metal centers is well-established, particularly for systems with N-donor ligands. In contrast, there are limited examples of intermolecular C—H bond activation at platinum(II) centers supported by phosphine donor ligands: these phosphine-supported systems require relatively high temperatures (125–150° C.). It is expected that the zwitterionic, complexes described herein, such as the bis (phosphino)borate platinum complexes, will promote transformations at C—H bonds. Furthermore, it is expected that such complexes will be soluble in relatively nonpolar media, in contrast to their discrete salt relatives Systems thus designed should be amenable to mechanistic study due to the presence of a useful spectroscopic $^{31}P$ NMR handle. In addition, designing systems that attenuate or eliminate counter-anion effects may provide an important mechanistic simplification.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

It must be noted that, as used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "suitable solvent" includes a single such solvent as well as a combination or mixture of different solvents, and the like.

In describing and claiming the present invention, the following terminology will be used in accordance with the definitions set out below.

As used herein, the term "alkyl" refers to a branched or unbranched saturated hydrocarbon group typically although not necessarily containing about 1–24 carbon atoms, unless indicated otherwise. Exemplary alkyl groups include methyl, ethyl, n-propyl, isopropyl, n-butyl, isobutyl, t-butyl, n-amyl, isoamyl, n-hexyl, n-heptyl, n-octyl, n-decyl, hexyloctyl, tetradecyl, hexadecyl, eicosyl, tetracosyl, and the like, as well as cycloalkyl groups such as cyclopropyl, cyclobutyl, cyclopentyl, cyclohexyl, cycloheptyl, cyclooctyl and the like. Generally, although again not necessarily, alkyl groups herein contain about 1–12 carbon atoms. The term "lower alkyl" refers to an alkyl group of 1–6 carbon atoms, preferably 1–4 carbon atoms. The alkyl group is optionally substituted at one or more positions. Exemplary substituents include but are not limited to hydroxyl, cyano, alkoxy, =O, =S, —$NO_2$, halo, heteroalkyl, amine, thioether, —SH, and aryl. Accordingly, if not otherwise indicated, the terms "alkyl" includes branched, unbranched, unsubstituted, and substituted alkyl groups. The term "cycloalkyl" refers to a cyclic alkyl, as defined above, and is typically a stable 3-to 7 membered monocyclic or 7-to 10-membered polycyclic ring which is saturated or partially unsaturated (e.g., containing one or more double bonds). Similarly, the term "cycloheteroalkyl" is intended to mean a cyclic alkyl group, as defined above, that contains one or more heteroatoms, and is typically a stable 3-to 7 membered monocyclic or 7-to 10-membered polycyclic ring which is saturated or partially unsaturated and contains 1–4 heteroatoms (N, O, S, P or Si). As with alkyl, the terms "cycloalkyl" and "cycloheteroalkyl" are intended to include both unsubstituted and substituted groups. The substitutions can be on a carbon or a heteroatom if the resulting compound is stable. For example, any amino group contained within the heterocycloalkyl group can be a primary, secondary or tertiary amine, as long as the structure is stable.

As used herein, the term "aryl" is intended to mean an aromatic substituent containing a single aromatic ring (e.g., phenyl) or multiple aromatic rings that are fused together (e.g., naphthyl or biphenyl), directly linked, or indirectly linked (such that the different aromatic rings are bound to a common group such as a methylene or ethylene moiety). Typically, the aryl group comprises from 5–14 carbon atoms. Preferred aryl groups contain one aromatic ring or two fused or linked aromatic rings, e.g., phenyl, naphthyl, biphenyl, diphenylether, diphenylamine, benzophenone, and the like. The aryl moiety may be independently substituted with one or more substituent groups, typically 1–3 substituents, including =O, —OH, —COOH, —$CH_2$—$SO_2$-phenyl, —$C_{1-6}$alkyl, —O—$C_{1-6}$alkyl, —C(O)—$C_{1-4}$alkyl, —$(CH_2)_{0-2}$—C(O)—O—$C_{1-4}$alkyl, cycloalkyl, —$C_{1-6}$alkoxy, halo, nitro, amino, alkylamino, dialkylamino, —C(O)—N($C_{1-4}$alkyl)$_2$, —NH—C(O) —$C_{1-4}$alkyl, —C(O)—$NH_2$, —$SO_2$—$NH_2$, trifluoromethyl, cyano, aryl, benzyl, —O—aryl and —S-aryl. Thus, the term "aryl" includes unsubstituted and substituted aryl groups. The term "heteroaryl" refer to aryl, as defined above, in which at least one carbon atom, typically 1–3 carbon atoms, is replaced with a heteroatom (N, O, S, P or Si). The heteroaryl can have the heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like). As with aryl, the term "heteroaryl" is intended to include both unsubstituted and substituted heteroaryl groups. The substitutions can be on a carbon or a heteroatom if the resulting compound is stable. For example, any amino group contained within the heteroaryl group can be a primary, secondary or tertiary amine, as long as the structure is stable.

The term "halo" is intended to represent a chloro (Cl), bromo (Br), fluoro (F) or iodo (I) substituent.

The term "heteroatom" refers to nitrogen, oxygen, sulfur, phosphorus and silicon. As a linker, the heteroatom is represented by —O—, —S—, —NR—, etc. The heteroatoms can exist in their chemically allowed oxidation states. Thus sulfur can exist as a sulfide, sulfoxide, or sulfone.

The term "ligand or the abbreviation "L" refers to a mono or bidentate, displaceable neutral donor ligand. Examples of such ligands include by way of illustration an not limitation, acetone, acetonitrile, olefin adducts, carbon monoxide, pyridine, tertiary phosphines, tertiary amines, diethyl ether, and so forth.

The term "pseudo-halide" or "pseudo-halo" refers to those compounds or substituents that behave as halides in their acid-base and redox chemistry. These include, by way of example, triflate (R—O—S(O)$_2$CF$_3$), acetates (R—O—C(O)CH$_3$), trifluoroacetate (R—O—C(O)CF$_3$), azide, cyanide and so forth.

In describing and claiming the present invention, the following abbreviations will be used in accordance with the definitions set out below.

| ABBREVIATIONS | |
|---|---|
| Ar | aryl |
| ASN | 5-azonia-spiro[4.4]nonane |
| ASNBr | 5-azonia-spiro [4.4]nonane bromide |
| n-BuLi | n-butyllithium |
| t-Bu | tert-butyl |
| COD | cyclooctadiene |
| DABCO | 1,4-diazabicyclo[2,2,2]octane |
| DCM | dichloromethane |
| dppp | 1,3-bis(diphenylphosphino)propane) |
| Et | ethyl |
| Et$_2$O | diethyl ether |
| Et$_3$N | triethylamine |
| EtOH | ethanol |
| L | mono or bidentate, displaceable neutral donor ligand |
| Me | methyl |
| NBD | norbornadiene |
| OTf | —O—S(O)$_2$CF$_3$ |
| Ph | phenyl |
| Ph$_2$BCl | diphenylchloroborane |
| RT | room temperature |
| THF | tetrahydrofuran |
| TMEDA | N,N,N',N'-tetramethylethylene-1,2-diamine |

One embodiment of the invention is a class of anionic borate ligands, which are compounds having the formula I:

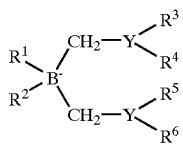

wherein:
$R^1$ and $R^2$ are independently selected from the group consisting of alkyl and aryl;

Y is selected from the group consisting of P and N; and $R^3$, $R^4$, $R^5$ and $R^6$ are independently selected from the group consisting of alkyl and aryl.

Exemplary compounds of formula I are described below. This list is intended to be illustrative and not limiting of the invention. The compounds are shown as $R^1$ and $R^2$ being the same substituent, and the $R^3$, $R^4$, $R^5$ and $R^6$ substituents being the same. It is understood however, that the invention also encompasses those compounds where $R^1$ and $R^2$ are different from each other, and the $R^3$, $R^4$, $R^5$ and $R^6$ substituents are different from each other.

TABLE 1

| Compound | $R^1$ and $R^2$ | Y | $R^3$, $R^4$, $R^5$ and $R^6$ |
|---|---|---|---|
| (I)1 | phenyl | P | phenyl |
| (I)2 | 3-methylphenyl | P | phenyl |
| (I)3 | 3-t-butylphenyl | P | phenyl |
| (I)4 | 3-methoxyphenyl | P | phenyl |
| (I)5 | 2,4-di(trifluoromethyl)-phenyl | P | phenyl |
| (I)6 | 1,2,3,4,5-pentafluorophenyl | P | phenyl |
| (I)7 | phenyl-d$_5$ | P | phenyl |
| (I)8 | phenyl | P | t-butyl |
| (I)9 | 3-t-butylphenyl | P | t-butyl |
| (I)10 | phenyl | P | methyl |
| (I)11 | phenyl | P | 3-t-butylphenyl |
| (I)12 | phenyl | P | 2,4-di(trifluoromethyl)-phenyl |
| (I)13 | phenyl | N | methyl |
| (I)14 | phenyl | N | isopropyl |
| (I)15 | phenyl | N | t-butyl |
| (I)16 | phenyl | N | phenyl |

The bis(phosphino) and bis(amino) borate ligands of the invention can be installed on a variety of metals centers. Accordingly, another embodiment of the invention pertains to a zwitterionic complex of the formula II:

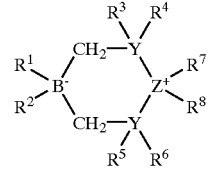

wherein:
$R^1$ and $R^2$ are independently selected from the group consisting of alkyl and aryl;

Y is selected from the group consisting of P and N; and $R^3$, $R^4$, $R^5$ and $R^6$ are independently selected from the group consisting of alkyl and aryl;

Z is a metal; and $R^7$ and $R^8$ are independently selected from the group consisting of halo, pseudo-halo, alkyl, aryl and mono or bidentate, displaceable neutral donor ligands.

Metals suitable for use in the zwitterionic complex of the invention include, by way of example and not limitation, metals from Group 4 of the Periodic Table of the Elements (titanium (Ti), zirconium (Zr), hafnium (HF)), from Group 7 of the Periodic Table of the Elements (manganese (Mn), rhenium (Re)), from Group 8 of the Periodic Table of the Elements (iron (Fe), ruthenium (Ru), osmium (Os)), from Group 9 of the Periodic Table of the Elements (cobalt (Co), rhodium (Rh), iridium (Ir)), from Group 10 of the Periodic Table of the Elements (nickel (Ni), palladium (Pd), platinum (Pt)), and aluminum (Al), can be used in the complex of the invention. Metals from Group 9 and Group 10 are particularly preferred, in particular, rhodium, nickel, palladium, and platinum.

Exemplary compounds of formula II are described below. This list is intended to be illustrative and not limiting of the invention. For compounds (II)1–12, $R^1$ and $R^2$ are phenyl; $R^3$, $R^4$, $R^5$ and $R^6$ are phenyl; and Y is P. For compound (II)13, $R^1$ and $R^2$ are phenyl; $R^3$, $R^4$, $R^5$ and $R^6$ are methyl; and Y is N.

TABLE II

| Compound | Z | $R^7$ | $R^8$ |
|---|---|---|---|
| (II)1 | Ni | chloro | chloro |
| (II)2 | Ni | methyl | chloro |
| (II)3 | Ni | chloro | L |
| (II)4 | Ni | L | L |
| (II)5 | Pd or Pt | chloro | chloro |
| (II)6 | Pd or Pt | methyl | methyl |
| (II)7 | Pd or Pt | R | chloro |
| (II)8 | Pd or Pt | R | L |
| (II)9 | Pd or Pt | L | L |
| (II)10 | Pd or Pt | -O-acetyl | -O-acetyl |
| (II)11 | Pd or Pt | OTf | OTf |
| (II)12 | Pd or Pt | OTf | L |
| (II)13 | Rh | L | L |

Another embodiment of the invention pertains to a zwitterionic complex of the formula III:

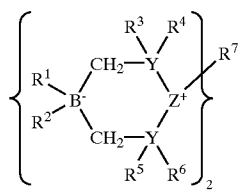

wherein:

$R^1$ and $R^2$ are independently selected from the group consisting of alkyl and aryl;

Y is selected from the group consisting of P and N; and $R^3$, $R^4$, $R^5$ and $R^6$ are independently selected from the group consisting of alkyl and aryl;

Z is a metal; and $R^7$ is selected from the group consisting of halo, pseudohalo, alkyl, aryl and mono or bidentate, displaceable neutral donor ligands.

Exemplary compounds of formula III are described below. This list is intended to be illustrative and not limiting of the invention. For all of the foregoing examples, $R^1$ and $R^2$ are phenyl; $R^3$, $R^4$, $R^5$ and $R^6$ are phenyl; and Y is P.

TABLE III

| Compound | Z | $R^7$ |
|---|---|---|
| (III)1 | Pd or Pt | chloro |
| (III)2 | Ni | methyl |
| (III)3 | Rh | L |

As noted above, the zwitterionic complexes of the invention find utility in numerous stoichiometric and catalytic applications, as will be described in detail below. Accordingly, one aspect of the invention is a method of catalyzing a reaction wherein transformation of a robust sigma bond in an organic compound is required, comprising: a) contacting the organic compound with i) an organic or inorganic reagent, and ii) a zwitterionic complex of an anionic borate ligand having the formula:

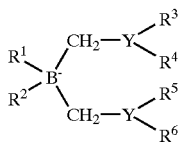

and a metal compound; wherein: $R^1$ and $R^2$ are independently selected from the group consisting of alkyl and aryl; Y is selected from the group consisting of P and N; and $R^3$, $R^4$, $R^5$ and $R^6$ are independently selected from the group consisting of alkyl and aryl; and b) producing an organic compound having a transformed robust sigma bond.

The robust sigma bond is an E—H bond, where E is C, B, Si, N, H or O. Thus, the organic compound used in the method will be a compound having at least one robust sigma bond, such as R—C—H, R—B—H, R—Si—H, R—N—H, H—H or R—O—H. The robust sigma bond is preferably a C—H bond.

It is expected that the zwitterionic complex of the invention will be useful in mediating transformations similar to their more traditional cationic relatives. The following reaction transformations are intended to be merely illustrative and not limiting of the applications to which these complexes can be utilized. The following transformations were selected because they rely upon many elementary organometallic processes including (i) solvent ligand dissociation, (ii) oxidative addition, (iii) olefin insertion, (v) β-hydride elimination, (vi) and reductive elimination. As the zwitterion of the invention has proved to be competent at mediating these reactions, comparative rate data between the zwitterion of the invention and their structurally related cations is obtainable.

Benzene C—H Activation

In one embodiment of the invention, the zwitterionic complex is used to mediate a benzene C—H activation process. Exemplary C—H bond activation reactions are shown below.

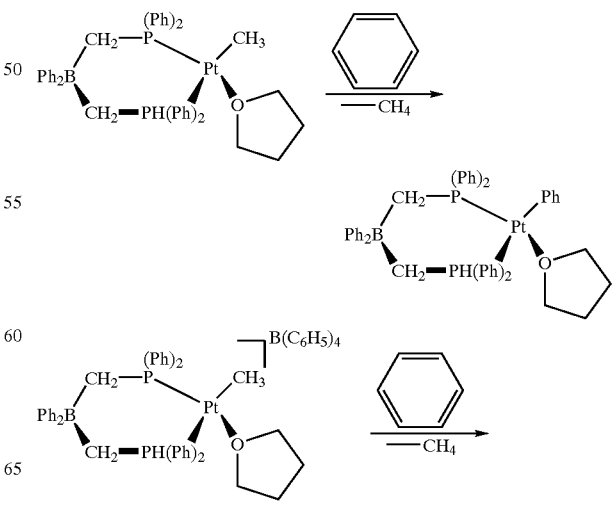

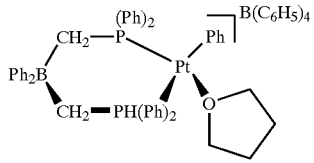

The term electrophilic activation has been widely used to describe a variety of late metal complexes that mediate C—H bond activation processes (Stahl at al., *Angew. Chem. Int. Edit.* 37: 2181 (1998)). An important issue to be resolved is whether these cationic systems mediate C—H activation processes because they are highly electrophilic, or simply because they have an exposed coordination site. A charge neutral, zwitterionic platinum(II) system supported by the [Ph$_2$B(CH$_2$PPh$_2$)$_2$]$^-$ ligand (Thomas et al., *J. Am. Chem. Soc.* 123:5100 (2001), as well as a cationic complex supported by Ph$_2$Si(CH$_2$PPh$_2$)$_2$, were prepared to address this question.

The main results are summarized as follows. Both the charge neutral platinum complex [Ph$_2$B(CH$_2$PPh$_2$)$_2$]Pt(Me)(THF) and the cationic complex [Ph$_2$Si(CH$_2$PPh$_2$)$_2$Pt(Me)(THF)][B(C$_6$F$_5$)$_4$] mediated a clean, pseudo-first order benzene C—H activation reaction at moderate temperature (~45° C.). Few phosphine-supported platinum(II) systems have been studied with respect to C—H activation processes; those that have been studied require much higher temperatures (~125° C.). For a related cationic system that requires high temperatures (>120° C.), see Peters et al., *Organometallics* 17:4493 (1998). Most significant is that the charge neutral zwitterionic complex of the invention mediates the bond activation reaction at an appreciably faster rate (~10-fold). The zwitterion shows a rather small deuterium isotope effect (k$_H$/k$_D$=1.25), clean pseudo-first order kinetics (k$_{obs}$=1.42(5)×10$^{-4}$s$^{-1}$ at 45° C.; t$_{1/2}$=81 minutes), and a large THF dependence. These data are consistent with a rate-limiting step dependent on THF loss. Kinetic studies of the cationic system revealed a much larger deuterium isotope effect (k$_H$/k$_D$=6.10). The distinctly different isotope effects observed may indicate that different rate-determining steps are operative in each system; oxidative C—H bond addition, rather than solvent loss, may be rate-determining in the cationic system.

This experiment suggests that electrophilic C—H activation may not be the best description for a C—H activation process mediated by platinum(II), at least for phosphine donor ligand systems. Studies of cationic dimmine platinum complexes indicate that a more electron-rich complex will mediate a benzene C—H activation process at a faster rate (Zhong et al., *J. Am. Chem. Soc.* 124(7)1378–1399 (2002)).

Polymerization

In another embodiment of the invention, the zwitterionic complex is used to catalyze a polymerization reaction. For example, the polymerization reaction can be the copolymerization of ethylene and carbon monoxide to yield —[(CH$_2$)$_2$—(CO)]$_n$—.

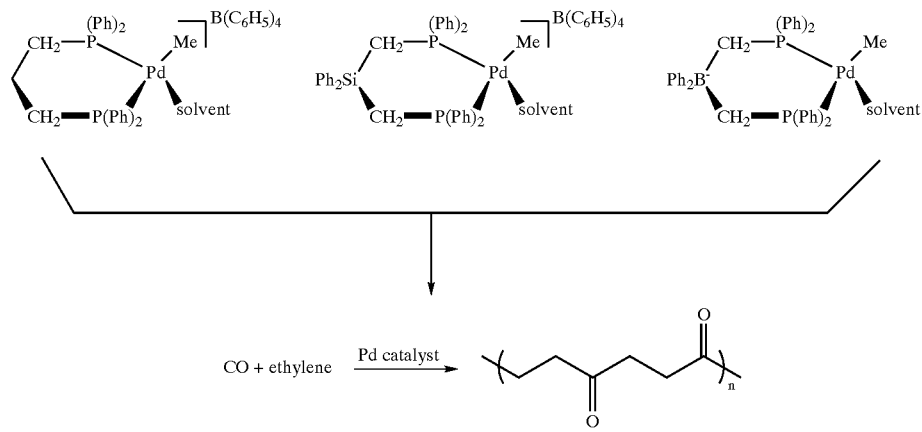

It is known that cationic palladium(II) complexes supported by chelating phosphines are able to mediate the strictly alternating copolymerization of carbon monoxide and ethylene to generate polyketone polymer (Drent et al., *Chem. Rev.* 96:663 (1996)). The zwitterions of the invention also mediate this polymerization reaction.

[Ph$_2$B(CH$_2$PPh$_2$)$_2$]Pd(Me)(THF) was prepared and its reactivity measured under a pressure of CO and ethylene. This system serves as a charge neutral relative to the prototypical, cationic catalyst system [(dppp)Pd(Me)(solv)]$^+$. The zwitterionic Pd(II) complex, [Ph$_2$B(CH$_2$PPh$_2$)$_2$]Pd(Me)(THF), was found to be a very active catalyst for the copolymerization of CO and ethylene at ambient temperature and afforded clean, strictly alternating polyketone (MW~138,000; Mn~112,000; PDJ=1.25). In a comparative study this zwitterion was shown to be as efficient a catalyst as structurally related cationic systems, as reported in Lu et al., *J. Amer. Chem. Soc.* 124(19):5272–5273 (2002).

The olefin adduct [Ph$_2$B(CH$_2$PPh$_2$)$_2$]Pd(CH$_3$)(CH$_2$=CH$_2$) can be formed cleanly at low temperature under excess ethylene. Its first order decay was measured to compare its rate of ethylene insertion with [(dppp)Pd(Me)(CH$_2$=CH$_2$)][B(3,5-(CF$_3$)$_2$—C$_6$H$_3$)$_4$]. Within experimental error, the insertion rate obtained for [Ph$_2$B(CH$_2$PPh$_2$)$_2$]Pd(CH$_3$)(CH$_2$=CH$_2$) was equal to that reported for [(dppp)Pd(Me)(CH$_2$=CH$_2$)][B(3,5-(CF$_3$)$_2$—C$_6$H$_3$)$_4$] at −47° C. in CH$_2$Cl$_2$. This result is surprising given the presumed difference in electrophilicity between the two systems. Moreover, this experiment introduces the notion that the zwitterions of the invention may serve to mediate rapid olefin insertion rates when cationic, isostructural complexes are already known to do so.

Catalytic Addition of H—E Bonds to Olefins and Alkynes

In another embodiment of the invention, the zwitterionic complex is used to catalyze the addition of E—H bonds to olefins and alkynes, where the E—H bond is selected from the group consisting of H—H, Si—H, B—H, C—H, and N—H. Three exemplary E—H addition reactions to olefins are illustrated below.

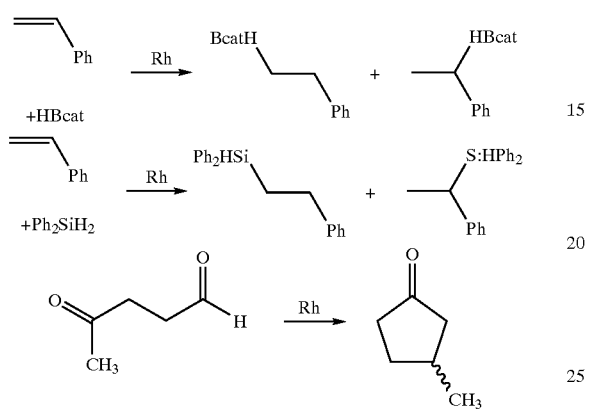

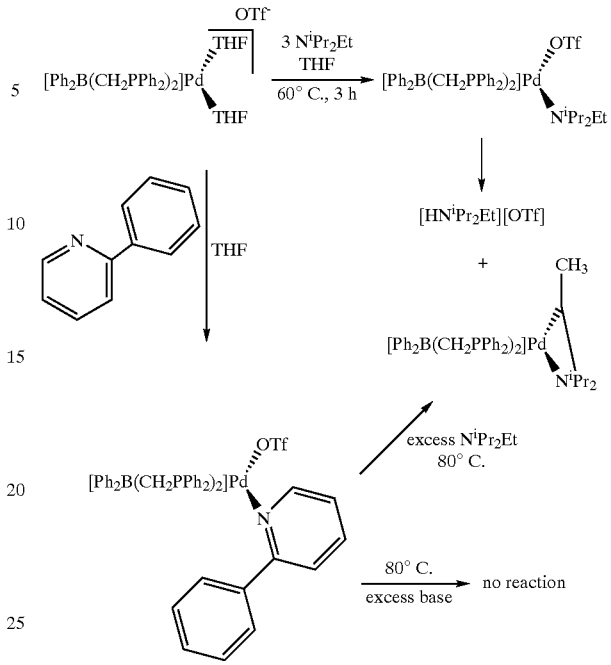

A series of zwitterionic complexes including the phosphine-based systems $[Ph_2B(CH_2PPh_2)_2]Rh$ (norbornadiene) and $[Ph_2B(CH_2PPh_2)_2]Rh(solvent)_2$, and the nitrogen-based systems $[Ph_2BN^{Me}{}_2]Rh(norbornadiene)$ and $[Ph_2BN^{Me}{}_2]Rh(solvent)_2$ were prepared. These systems give rise to rapid catalytic processes including hydrogenation, hydrosilation, hydroboration, and hydroacylation reactions (see above), transformations also mediated by their traditional cationic counter-parts. Interestingly, the neutral zwitterions are active catalysts even with acetonitrile as the solventodonor ligand: Acetonitrile typically poisons cationic systems by tying up a required substrate coordination site (Bosnich et al., *Acc. Chem. Res.* 31:667 (1998)). For example, the zwitterionic complex $[Ph_2B(CH_2PPh_2)_2]Rh$ $(CH_3CN)_2$ rapidly hydroacylates 4-methyl-4-pentenal to quantitatively produce 3-methylcyclopentanone as a racemic mixture (0.2 mol % catalyst, THF, 25° C., 30 min). The related cationic systems $[Ph_2Si(CH_2PPh_2)_2$ and $[Ph_2Si(CH_2PPh_2)_2Rh(acetone)_2][B(C_6F_5)_4]$ show very poor activity under similar conditions; $[Ph_2Si(CH_2PPh_2)_2$ $Rh(CH_3CN)_2][B(C_6F_5)_4]$ is completely inactive while $[Ph_2Si(CH_2PPh_2)_2Rh(acetone)_2][B(C_6F_5)_4]$ is extremely sluggish, even at 25 mol %.

These results suggest that the zwitterionic complex of the invention systems is likely to be less sensitive to polar donor solvents or functionalities that might otherwise attenuate, or completely inhibit, catalytic activity in typical cationic systems.

Selective Activation of SP³-Hybridized Bonds

In another embodiment of the invention, the zwitterionic complex is used to selectively activate sp³-hybridized C—H bonds. This is illustrated below for the selective activation of sp³-hybridized C—H bonds α to tertiary amine N atoms.

In the course of exploring amine base "promoted" strategies to C—H bond activation chemistry at platinum, it was found that the zwitterionic complex $[Ph_2B(CH_2PPh_2)_2]Pd$ (OTf)(THF), which in THF equilibrates with the disolvento species $[Ph_2B(CH_2PPh_2)_2]Pd(THF)2][OTf]$, underwent a C—H bond activation reaction 60° C. with tertiary amines to cleanly generate a novel organometallic product in which the carbon atom α to the amine nitrogen had lost a proton and was replaced by palladium. A stoichiometric equivalent of ammonium triflate was trapped in the reaction. Most intriguing was the selectivity of the C—H activation process for sp³-hybridized C—H bonds α to a tertiary amine.

It is expected that the zwitterionic complex will also serve to catalyze the procedure for functionalizing tertiary amines at the α C—H position.

Organic Transformation

In another embodiment of the invention, the zwitterionic complex is used to catalyze an organic transformation reaction. The examples set forth above fall into this category, such as the catalytic addition of E—H bonds to olefins and alkynes.

Alkane Activation

In another embodiment of the invention, the zwitterionic complex is used to catalyze an alkane activation reaction. Examples of such reactions include palladium and platinum catalyzed C—H activation reactions.

Alkane Functionalization

In another embodiment of the invention, the zwitterionic complex is used to catalyze an alkane functionalization reaction. An example of an alkane functionalization reaction is an alkane oxidative reaction.

In addition to the reactions described above, the zwitterionic complex of the invention finds utility in the improved synthesis of numerous compounds, and pharmaceutical agents in particular, that are synthesized by methods utilizing traditional metal catalysts such as a Pd—C catalyst, a Raney-Ni catalyst, a Pt catalyst, a Pd—C catalyst, and so forth.

EXAMPLES

The practice of the present invention will employ, unless otherwise indicated, conventional techniques of pharmaceutical formulation, medicinal chemistry, and the like, which are within the skill of the art. Such techniques are explained fully in the literature.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All components were obtained commercially unless otherwise indicated.

Materials and Methods

Unless otherwise noted, all syntheses were carried out in the absence of water and dioxygen, using standard Schlenk and glovebox techniques. THF, $Et_2O$, petroleum ether, DCM, acetonitrile, toluene, and benzene were deoxygenated and dried by thorough sparging with $N_2$ gas followed by passage through an activated alumina column and were stored over 3 Å molecular sieves. For the Pt compounds, pentane, hexanes, and EtOH were deoxygenated by repeated evacuation under reduced pressure followed by introduction of dinitrogen and were dried by storing over 3 Å molecular sieves. For the Rh compounds, EtOH and methanol were distilled under vacuum after stirring over $CaH_2$ for 24 h. Nonhalogenated solvents were typically tested with a standard solution of sodium benzophenone ketyl in tetrahydrofuran in order to confirm effective oxygen and moisture removal. Deuterated chloroform, benzene, DCM, acetonitrile, and acetone were purchased from Cambridge Isotope Laboratories, Inc. and were degassed by repeated freeze-pump-thaw cycles and dried over activated 3 Å molecular sieves prior to use. $B(C_6F_5)_3$ was recrystallized from pentane at −35 ° C. prior to use. $(COD)Pt(Cl)_2$ (Clark et al., J. Organomet. Chem 59:411–428 (1973)), (COD)Pt(Me)(Cl) (Clark et al., J. Organomet. Chem 59:411–428 (1973)), $(COD)Pt(Me)_2$ (Costa et al., M.Inorg. Syn. 31:284–286 (1995)), $Ph_2BCl$ (Treichel et al., Inorg. Syn. 13:32–38 (1973)), $Ph_2PMe$ (Seyferth et al., J. Org. Chem. 28:2463–2464 (1963)), $Ph_2PCH_2Li(TMEDA)$ (Schore et al., Inorg. Chem. 20:3200–3208 (1981)), and 5-azonia-spiro[4,4]nonane bromide (Blicke et al., J. Org. Chem. 76:5099–5103 (1954)) were prepared by the noted literature methods.

$[^iPr_2EtNH][BPh_4]$ was prepared by acidifying an aqueous solution of $^iPr_2EtN$ and $NaBPh_4$ with aqueous HCl. (COD)Pt(Me)(Ph) (Clark et al.,J. Organomet. Chem. 101:347–358 (1975); Hackett et al., Organometallics 6:403–410 (1987)) was prepared by addition of PhMgBr to a cold (−35° C.) DCM solution of (COD)Pt(Me)(Cl). All other chemicals were purchased from Aldrich, Strem, Alfa Aesar, or Pressure Chemicals and used without further purification.

NMR spectra were recorded at ambient temperature on Varian Mercury 300 MHz and Inova 500 MHz, and Joel 400 MHz spectrometers, unless otherwise noted. $^1H$ and $^{13}C$ NMR chemical shifts were referenced to residual solvent. For the Pt compounds, $^{31}P$ NMR and $^{11}B$ NMR chemical shifts are reported relative to an external standard of 85% $H_3PO_4$ or neat $BF_3.Et_2O$ respectively. For the Rh compounds, $^{31}P$ NMR, $^{11}B$ NMR, and $^{19}F$ NMR chemical shifts are reported relative to an external standard of 85% $H_3PO_4$, neat $BF_3.Et_2O$, and neat $CFCl_3$ respectively. IR spectra were recorded on a Bio-Rad Excalibur FTS 3000 spectrometer controlled by Win-IR Pro software. Elemental Analyses were performed by Desert Analytics, Tucson, Ariz. X-ray diffraction experiments were carried out by the Beckman Institute Crystallographic Facility on a Bruker Smart 1000 CCD diffractometer. MS data for samples were obtained by injection of an acetonitrile solution into a Hewlett Packard 1100MSD Mass Spectrometer ($ES^+$) or an Agilent 5973 Mass Selective Detector (EI). Deuterated solvents were degassed and dried over activated 3-Å molecular sieves prior to use.

General Method for Preparation of Borane Synthons

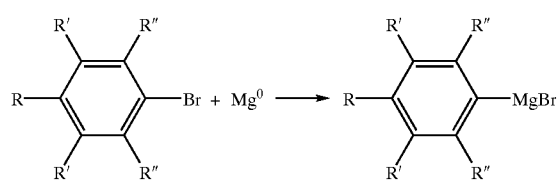

-continued

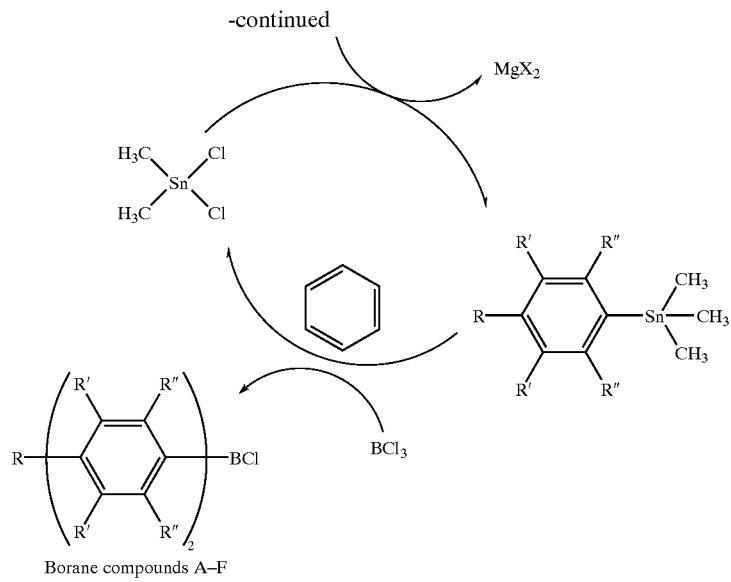

Borane compounds A–F

Borane compounds A through F have the following substituents:

| | |
|---|---|
| A | R = R' = R" = F |
| B | R' = R" = H; R = Me |
| C | R' = R" = H; R = Butyl |
| D | R' = R" = H; R = OMe |
| E | R' = R" = H; R = CF$_3$ |
| F | R = R" = H; R' = CF$_3$ |

General Method of Formation for Anionic Borate Ligands

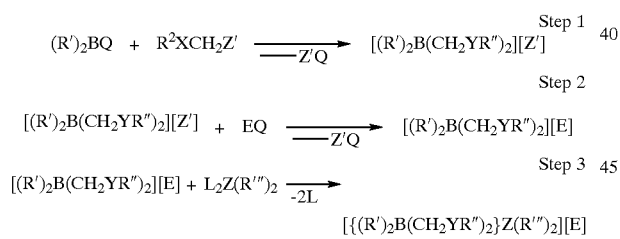

where:
- R' is alkyl or aryl. Each R' may be the same or different. The aryl can be substituted such as p-MeOPh, p-MePh, p-t-BuPh.
- Q is a halide, triflate, acetate or other labile leaving group.
- Y is P or N;
- R" is alkyl or aryl. Each R" may be the same or different. Examples include Ph and t-Bu.
- Z' is an alkali metal cation such as Li, Na, K or MgQ.
- E is an alkali metal cation of the formula R$_4$N$^+$.
- L is a mono or bidentate, displaceable neutral donor ligand
- Z is a metal. Examples include Ni, Pd and Pt.
- R'" is halo, pseudo-halo, alkyl or aryl. Each R'" may be the same or different.

Illustrated graphically, the resulting anionic borate ligand product from Step 3, has the formula:

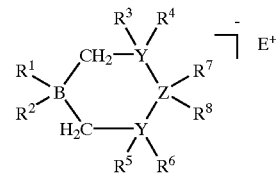

EXAMPLE 1

Synthesis of [Ph$_2$B(CH$_2$Ph$_2$)$_2$][ASN] (1)

Synthesis of (1) was readily achieved by low-temperature addition of a toluene solution of diphenylchloroborane to a Et$_2$O solution of Ph$_2$PCH$_2$Li(TMEDA). This generates [Ph$_2$B(CH$_2$PPh$_2$)$_2$][Li(TMEDA)$_2$], whose structure is shown below. Cation exchange provided the ASN salt (1) in high yield. Details of the synthesis are as follows.

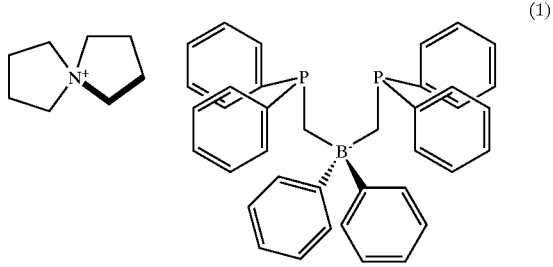

(1)

Solid yellow Ph$_2$PCH$_2$Li(TMEDA) (4.82 g, 15.0 mmol) was dissolved in Et$_2$O (180 mL)in a Schlenk flask with a stir bar and sealed with a septum. The reaction vessel was cooled to −78° C. in a dry ice/acetone bath. Ph$_2$BCl (1.514 g, 7.553 mmol), dissolved in toluene (10 mL),was introduced dropwise via syringe to the cooled reaction flask. The reaction was stirred and warmed gradually to RT over 14 h, providing a pale yellow precipitate. Volatiles were removed in vacuo, and the resulting solids were isolated in a drybox on a sintered glass frit and washed with Et$_2$O (5×10 mL). Drying in vacuo provided pale yellow solid [Ph$_2$B(CH$_2$PPh$_2$)$_2$][Li (TMEDA)$_2$] (5.67 g). Crystals suitable for an X-ray diffraction experiment were grown by slowly cooling a hot toluene solution of [Ph$_2$B(CH$_2$PPh$_2$)$_2$][Li(TMEDA)$_2$]. Solid [Ph$_2$B(CH$_2$PPh$_2$)$_2$][Li(TMEDA)$_2$] was dissolved in EtOH (40 mL).

[Ph$_2$B(CH$_2$PPh$_2$)$_2$][Li(TMBDA)$_2$]: (C$_{50}$H$_{65}$BLiN$_4$P$_2$), MW=801.75, colorless prism, collection temperature=98° K., monoclinic, space group=P2$_1$/c, a=11.7922(6) Å, b=11.7081(6) Å, c=33.1336(18) Å, α=90°, β=94.0620(10)°, γ=90°, V=4563.1(4) Å$^3$, Z=4, R$_1$=0.061 [I>2σ(I)], GOF=1.952.

ASNBr (1.8 g, 8.7 mmol)was dissolved in EtOH (8 mL)and added to stirring (1). A white precipitate formed immediately. The mixture was stirred for 10 min, and white solids were subsequently collected by filtration. The solids were washed with EtOH (2×10 mL) and Et$_2$O (3×10 mL) and dried in vacuo for 24 h, providing (1) as a pure, white solid (4.30 g, 6.23 mmol, 83.1%).

$^1$H NMR (300 MHz,d$_6$-acetone): δ=7.29 (b, 4H, ortho B(C$_6$H$_5$)$_2$), δ=7.17 (m, 8H, ortho P(C$_6$H$_5$)$_2$), δ=7.00 (m, 12H, meta B(C$_6$H$_5$)$_2$ and P(C$_6$H$_5$)$_2$), δ=6.74 (m, 4H, para P(C$_6$H$_5$)$_2$), δ=6.62 (m, 2H, para B(C$_6$H$_5$)$_2$), δ=3.65 (m, 8H, ((CH$_2$CH$_2$)$_2$)$_2$N), δ=2.23 (m, 8H, ((CH$_2$CH$_2$)$_2$)$_2$N), δ=1.64 (b, 4H, Ph$_2$B(CH$_2$PPh$_2$)$_2$). $^{13}$C{$^1$H}NMR (125.7 MHz,d$_6$-acetone): δ=165 (b, ipso B(C$_6$H$_5$)$_2$), δ=147.4 (d, ipso P(C$_6$H$_5$)$_2$, $^1$J$_{P-C}$=22 Hz), δ=134.7 (s, ortho B(C$_6$H$_5$)$_2$), δ=133.6 (d, ortho P(C$_6$H$_5$)$_2$, $^2$J$_{P-C}$=19 Hz), δ=127.1 (s, meta P(C$_6$H$_5$)$_2$, $^3$J$_{P-C}$=6 Hz), δ=126.0 (s, para P(C$_6$H$_5$)$_2$), δ=125.3 (s, meta B(C$_6$H$_5$)$_2$), δ=121.5 (s, para B(C$_6$H$_5$)$_2$), δ=63.1 (((CH$_2$CH$_2$)$_2$)$_2$N), δ=25.7 (b, [Ph$_2$B(CH$_2$PPh$_2$)$_2$]), δ=22.1 (((CH$_2$CH$_2$)$_2$)$_2$N). $^{31}$P{$^1$H}NMR (121.4 MHz,d$_6$-acetone): δ=−8.78 ($^2$J$_{P-B}$=10.0 Hz). $^{11}$B{$^1$H}NMR (128.3 MHz,d$_6$-acetone): δ=−12.6. Anal. Calcd. for C$_{46}$H$_{50}$BNP$_2$: C, 80.11; H, 7.31; N, 2.03. Found: C, 79.89; H, 7.45; N, 2.15.

EXAMPLE 2

Synthesis of [{Ph$_2$B(CH$_2$PPh$_2$)$_2$}Pt(Me)$_2$][ASN] (2) and [{Ph$_2$B(CH$_2$PPh$_2$)$_2$}Pt(Me)(Ph)][ASN] (3)

Reaction of (1) with either (COD)Pt(Me)$_2$ or (COD)Pt(Me)(Ph) in THF forms the anionic platinum(II) precursors [{Ph$_2$B(CH$_2$PPh$_2$)$_2$}Pt(Me)$_2$][ASN] (2) and [{Ph$_2$B(CH$_2$PPh$_2$)$_2$}Pt(Me)(Ph)][ASN] (3) in high yield. Details of the synthesis are as follows.

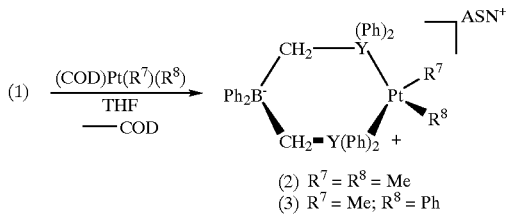

(2) R$^7$ = R$^8$ = Me
(3) R$^7$ = Me; R$^8$ = Ph

[Ph$_2$B(CH$_2$PPh$_2$)$_2$Pt(CH$_3$)$_2$][ASN] (2)

Solid (1) (391.8 mg, 0.5680 mmol)was suspended in THF (6 mL). A solution of (COD)Pt(Me)$_2$ (189.3 mg, 0.5679 mmol) in THF (2 mL) was added to the suspension, and the reaction homogenized as it stirred. A white precipitate formed after 1 h. The resulting mixture was concentrated in vacuo and triturated with pentane (2×2 mL). The off white solids were dried in vacuo, providing (2) as an off-white solid (511.2 mg,98.4%). Crystals suitable for X-ray diffraction were grown from slow evaporation of an acetonitrile solution of (2).

$^1$H NMR (300 MHz,d$_6$-acetone): δ=7.40 (m, 8H, P(C$_6$H$_5$)$_2$), δ=7.07 (m, 12H, B(C$_6$H$_5$)$_2$, (P(C$_6$H$_5$)$_2$)$_2$), δ=6.88 (m, 4H, B(C$_6$H$_5$)$_2$), δ=6.64 (m, 4H, para-(P(C$_6$H$_5$)$_2$)$_2$), δ=6.58 (m, 2H, para-B(C$_6$H$_5$)$_2$), δ=3.71 (m, 8H, ((CH$_2$CH$_2$)$_2$)$_2$N), δ=2.26 (m, 8H, ((CH$_2$CH$_2$)$_2$)$_2$N), =1.98 (b, 4H, Ph$_2$B(CH$_2$PPh$_2$), =0.08 (t, 6H, Pt(CH$_3$) $^3$J$_{P-H}$=12 Hz, $^2$J$_{Pt-H}$=68 Hz). $^{13}$C{$^1$H}NMR (125.7 MHz,d$_6$-acetone): δ=167 (b, ipso B(C$_6$H$_5$)$_2$), δ=140.1 (d, ipso P(C$_6$H$_5$)$_2$, $^1$J$_{P-C}$=39.0 Hz), δ=134.4 (m, ortho P(C$_6$H$_5$)$_2$), δ=133.5 (s, ortho B(C$_6$H$_5$)$_2$), δ=128.2 (s, meta B(C$_6$H$_5$)$_2$), δ127.3 (m, meta P(C$_6$H$_5$)$_2$), δ=126.3 (m, para P(C$_6$H$_5$)$_2$), δ=122.0 (s, para B(C$_6$H$_5$)$_2$), δ=63.7 (((CH$_2$CH$_2$)$_2$)$_2$N), δ=22.9 (b, [Ph$_2$B(CH$_2$PPh$_2$)$_2$]), δ=22.8 (((CH$_2$CH$_2$)$_2$)$_2$N), δ=5.5 (dd, Pt(CH$_3$)$_2$, $^1$J$_{Pt-C}$=600 Hz, $^2$J$_{P-C}$=103 Hz, $^2$J$_{P-C}$=9.1 Hz). $^{31}$P{H}NMR (121.4 MHz,d$_6$-acetone): δ=20.60 ($^1$J$_{Pt-P}$=1892 Hz). $^{11}$B{$^1$H}NMR (128.3 MHz,d$_6$-acetone): δ=−13.7. Anal. Calcd. for C$_{48}$H$_{56}$BNP$_2$Pt: C, 63.02; H, 6.17; N, 1.53. Found: C, 62.97; H, 5.90; N, 1.81.

[Ph$_2$B(CH$_2$PPh$_2$)$_2$Pt(CH$_3$)(C$_6$H$_5$)][ASN] (3)

A THF solution (1 mL) of (COD)Pt(Me)(Ph)(70.6 mg, 0.179 mmol) was added to a stirring suspension of (1) (123.1 mg, 0.1785 mmol) in THF (2 mL). The reaction was stirred for 30 min and became homogeneous. The solution was concentrated in vacuo, and off-white solids were precipitated with Et$_2$O (2 mL). The supernatant was removed, and the solids were washed with EtOH (2×2mL) and Et$_2$O (2×2 mL) and dried in vacuo, producing off-white (3) (122.4 mg, 70.2%).

$^1$H NMR (300 MHz,d$_6$-acetone): δ=7.47 (m, 4H), δ=7.24 (m, 4H), δ=7.12 (m, 2H), δ=7.09 (m, 4H), δ=6.98 (m, 4H), δ=6.87 (m, 8H), δ=6.62 (m, 4H), δ=6.57 (m, 2H), δ=6.43 (m, 2H), δ=6.29 (m, 1H, para Pt-C$_6$H$_5$), δ=3.69 (m, 8H, ((CH$_2$CH$_2$)$_2$)2N), δ2.26 (m, 8H, ((CH$_2$CH$_2$)$_2$)$_2$N), δ=2.10 (b, Ph$_2$B(CH$_2$PPh$_2$)$_2$), δ=2.02 (b, Ph$_2$B(CH$_2$PPh$_2$)$_2$), δ=0.08 (dd, 3H, Pt(CH$_3$), $^3$J$_{P-H}$(cis)=6.9 Hz, $^3$J$_{P-H}$(trans)=7.8 Hz, $^2$J$_{Pt-H}$=69 Hz). $^{13}$C{$^1$H}NMR (125.7 MHz,d$_6$-acetone): δ=166 (b, ipso B(C$_6$H$_5$)$_2$), δ=144 (b, ipso Pt(C$_6$H$_5$)), δ=140.5 (d, ipso P(C$_6$H$_5$)$_2$, $^1$J$_{P-C}$=39.5 Hz), δ=139.8 (d, ipso P(C$_6$H$_5$)$_2$, $^1$J$_{P-C}$=22.5 Hz), δ=138.7 (s, ortho Pt(C$_6$H$_5$) $^1$J$_{Pt-C}$=32 Hz), δ=135.0 (m, ortho P(C$_6$H$_5$)$_2$), δ=134.7 (m, ortho P(C$_6$H$_5$)$_2$), δ133.8 (s, ortho B(C$_6$H$_5$)$_2$), δ=128.9 (s, meta P(C$_6$H$_5$)$_2$), δ=128.4 (s, meta P(C$_6$H$_5$)$_2$), δ=127.9 (d, para P(C$_6$H$_5$)$_2$, $^4$J$_{P-C}$=8.5 Hz), δ=127.5 (d, para P(C$_6$H$_5$)$_2$, $^4$J$_{P-C}$=8.5 Hz), δ=127.0 (s, meta Pt(C$_6$H$_5$)), δ=126.8 (s, meta B(C$_6$H$_5$)$_2$), δ=122.4 (s, para B(C$_6$H$_5$)$_2$), δ=120.0 (s, para Pt(C$_6$H$_5$)), δ=64.3 (((CH$_2$CH$_2$)$_2$)$_2$N), δ=23.3 (((CH$_2$CH$_2$)$_2$)$_2$N), δ=23 (b, [Ph2B(CH$_2$PPh$_2$)$_2$]), δ=22 (b, [Ph$_2$B(CH$_2$PPh$_2$)$_2$]), δ=5.5 (dd, Pt—CH$_3$, $^2$J$_{P-C}$(trans)=93 Hz). $^{31}$P{$^1$H}NMR (121.4 MHz,d$_6$-acetone): δ=18.3 (d, $^1$J$_{Pt-P}$=1775 Hz, $^2$J$_{P-P}$=19 Hz), δ=17.29 (d, $^1$J$_{Pt-P}$=1868 Hz, $^2$J$_{P-P}$=19 Hz). $^{11}$B{$^1$H}NMR (128.3 MHz,d$_6$-acetone): δ=−13.8. Anal. Calcd. for C$_{53}$H$_{57}$BNP$_2$Pt: C, 65.16; H, 5.98; N, 1.43. Found: C, 64.90; H, 6.05; N, 1.54.

EXAMPLE 3

Synthesis of Ph$_2$B(CH$_2$PPh$_2$)$_2$Pt(CH$_3$)(THF) (4)

To generate the key neutral platinum complex, {Ph$_2$B(CH$_2$PPh$_2$)$_2$}Pt(Me)(L), several strategies were surveyed including protonolysis by acid and methide abstraction by B(C$_6$F$_5$)$_3$. All of these strategies effected the removal of one methyl group from (2), as determined by $^{31}$P NMR spectroscopy; however, most routes did not enable the clean isolation of a {Ph$_2$B(CH$_2$PPh$_2$)$_2$}Pt(Me)(L) complex. It was discovered that protonation of (2) in THF with the bulky ammonium salt [$^i$Pr$_2$EtNH][BPh$_4$] did enable both the clean generation of {Ph$_2$B(CH$_2$PPh$_2$)$_2$}Pt(Me)(THF) (4) and its isolation. The salt byproduct, [ASN][BPh$_4$], precipitated from THF and was readily removed. Solid (4) can be subsequently isolated by rapid precipitation from THF with pentane, a procedure that also removes the neutral amine byproduct, $^i$Pr$_2$EtN. It is noteworthy that the protonation of (2) directly contrasts with the reactivity of a related compound, (dppp)PtMe$_2$, which did not exhibit reactivity with [$^i$Pr$_2$EtNH][BPh$_4$] at 50° C. in THF solution over 24 h. Details of the synthesis are as follows.

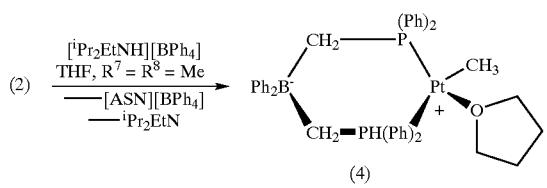

Solid (2) (49.3 mg, 53.9 tmol) was dissolved in THF (2 mL). A THF solution (1 mL) of [$^i$Pr$_2$EtNH][BPh$_4$] (24.3 mg, 54.1 μmol) was added to the stirring solution of (2). The clear, colorless reaction rapidly produced a white precipitate. The mixture was stirred for 15 min, and the white solids (ASNBPh$_4$) were filtered away. The solution was concentrated in vacuo, and pentane (2 mL) was added, precipitating solid (4) as a spectroscopically pure solid. The solid was collected by filtration. Due to the lability of the coordinated THF molecule, obtaining satisfactory combustion analysis was problematic.

$^1$H NMR (300 MHz, C$_6$D$_6$): δ=7.64 (m, 4H, aryl protons), δ=7.48 (m, 4H, aryl protons), δ=7.24 (m, 4H, aryl protons), δ=7.00 (m, 18H, aryl protons), δ=2.90 (b, 4H, Pt—O(CH$_2$CH$_2$)$_2$), δ=2.51 (d, 2H, Ph$_2$B(CH$_2$PPh$_2$)$_2$, $^2$J$_{P-H}$=18 Hz), δ2.37 (d, 2H, Ph$_2$B(CH$_2$PPh$_2$)$_2$, $^2$J$_{P-H}$=14 Hz), δ=0.71 (b, 4H, Pt—O(CH$_2$CH$_2$)$_2$), δ=0.35 (bd, 3H, Pt—CH$_3$, $^3$J$_{P-H}$=6 Hz, $^2$JP$_{t-H}$=40 Hz). $^{13}$C{$^1$H}NMR (125.7 MHz, THF, −5° C.): δ=160.3 (b, ipso B(C$_6$H$_5$)$_2$), δ134.1 (d, ispo P(C$_6$H$_5$)$_2$, $^1$J$_{P-C}$=42.1 Hz), δ=130.9 (d, ortho P(C$_6$H$_5$)$_2$, $^2$J$_{P-C}$=11.2 Hz), δ=130.8 (d, ortho P(C$_6$H$_5$)$_2$, $^2$J$_{P-C}$=10.7 Hz), δ=130.1 (d, ipso P(C$_6$H$_5$)$_2$, $^1$J$_{P-C}$=32.6 Hz), δ=129.7 (s, ortho B(C$_6$H$_5$)$_2$), δ=127.3 (s, meta P(C$_6$H$_5$)$_2$), δ=126.9 (s, meta P(C$_6$H$_5$)$_2$), δ=125.5 (d, para P(C$_6$H$_5$)$_2$, $^4$J$_{P-C}$=9.1 Hz), δ=125.1 (d, para P(C$_6$H$_5$)$_2$, $^4$J$_{P-C}$=11.2 Hz), δ=123.5 (s, meta B(C$_6$H$_5$)$_2$), δ=119.2 (s, para B(C$_6$H$_5$)$_2$), δ=64.9 (Pt—O(CH$_2$CH$_2$)$_2$), δ=22.6 (Pt—O(CH$_2$CH$_2$)$_2$), δ=21.2 (b, [Ph$_2$B(CH$_2$PPh$_2$)$_2$]), δ=15.3 (b, [Ph$_2$B(CH$_2$PPh$_2$)$_2$]), δ=8.2 (dd, Pt—CH$_3$, $^2$J$_{P-C}$(trans)=85.5 Hz, $^2$J$_{P-C}$(cis)=4.8 Hz). $^{31}$P{$^1$H}NMR (121.4 MHz, THF): δ=33.44 ($^1$J$_{Pt-P}$=1820 Hz, $^2$J$_{P-P}$=22 Hz), δ=15.96 ($^1$J$_{Pt-P}$=4478 Hz, $^2$J$_{P-P}$=22 Hz). $^{11}$B{$^1$H}NMR (128.3 MHz, THF): δ=−14.5.

An X-ray diffraction study on single crystals of (4) confirmed its structural assignment: (4)·2(THF) (C$_{43}$H$_{45}$BOP$_2$Pt.2(C$_4$H$_8$O)), MW=845.67×2(72.10), colorless block, collection temperature=98° K., triclinic, space group=P, a=12.210(4) Å, b=12.803(4) Å, c=16.205(5) Å, α=109.614(5)°, β=104.361(5)°, γ=96.489(5)°, V=2257.6 (12) Å$^3$, Z=2, R$_1$=0.043 [I>2σ(I)], GOF=1.404.

To date, this represents the third crystallographically characterized example of a platinum-THF adduct and is the only charge neutral species thus characterized for divalent platinum (Butts et al, *J. Am. Chem. Soc.* 118:11831–11843 (1996); Schlect et al., *Angew. Chem., Int. Ed. Engl.* 36:1994–1995 (1997)). Importantly, the coordinated THF molecule in (4) is weakly bound: it is readily substituted by a variety of neutral ligands (CO, pyridine, H$_2$O, acetone, Et$_3$N) and is very unstable under reduced pressure (placing (4) under vacuum leads to a single new product whose identity has yet to be determined). It should also be noted that (4) slowly degrades in THF solution at ambient temperature.

EXAMPLE 4

Generation of Ph$_2$B(CH$_2$PPh$_2$)$_2$Pt(C$_6$H$_5$)(THF) (5)

The ability of complex (4) to engage the aryl C—H bonds of benzene was examined. When a solid sample of (4) was dissolved and gently warmed in benzene, a solvent in which it is appreciably soluble, formation of one major product was observed. At 50° C., the reaction was complete after 4 h. The major product (80%) formed was {Ph$_2$B(CH$_2$PPh$_2$)$_2$}Pt(Ph)(THF) (5) based upon spectroscopic data. To confirm its assignment, (5) was independently generated by methide abstraction from (3) with B(Ar)$_3$ in THF. It is noted that addition of several molar equivalents of THF to a benzene solution of (4) slows the rate of benzene activation. The conversion of (4) to (5) occurs in greater yield in the presence of several molar equivalents of THF, albeit more slowly. Notably, H$_2$O has been observed to inhibit C—H activation in related systems by Tilset and co-workers (Heiberg et al., *J. Am. Chem. Soc.* 122:10831–10845 (2000)). Details of the reaction are as follows.

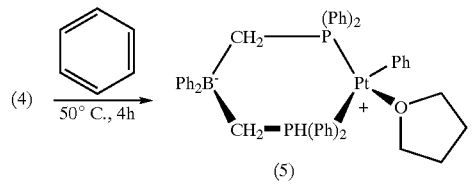

Solid (3) (23.6 mg, 24.2 μmol) was dissolved in THF (2 mL). Solid B(C$_6$F$_5$)$_3$ (12.5 mg, 24.4 μmol) was added to the stirring solution of (3). After 10 min, $^{31}$P NMR analysis showed the formation of one major product, consistent with the formulation of (5).

Solid (3) (51.4 mg, 52.6 μmol) was dissolved in THF (2 mL). A THF solution (2 mL) of [$^i$Pr$_2$EtNH][BPh$_4$] (23.5 mg, 52.3 μmol) was added to the stirring solution of (3). The clear, colorless reaction slowly produced a white precipitate. The mixture was stirred for 1 h, and the white solids were filtered away. The solution was concentrated in vacuo, and pentane (2 mL) was added, precipitating white solids. The solids were collected by filtration. NMR analysis of the solids was consistent with the formulation of (5) as the major product (~80%). Due to the lability of the coordinated THF molecule, obtaining satisfactory combustion analysis was problematic.

$^1$H NMR (300 MHz, C$_6$D$_6$): δ=7.56 (m, 4H, aryl protons), δ=7.46 (m, 4H, aryl protons), δ=7.21 (m, 4H, aryl protons), δ=6.95 (m, 18H, aryl protons), δ=6.88 (m, 2H, Pt(C$_6$H$_5$)), δ=6.78 (m, 2H, Pt-C$_6$H$_5$), δ=6.73 (m, 1H, para Pt-C$_6$H$_5$), δ=2.87 (b, 4H,Pt—O(CH$_2$CH$_2$)$_2$), δ=2.64 (d, 2H, Ph$_2$B(CH$_2$PPh$_2$)$_2$, $^2$J$_{P-H}$=17 Hz), δ=2.42 (d, 2H, Ph$_2$B(CH$_2$PPh$_2$)$_2$, $^2$J$_{P-H}$=14 Hz), δ=0.46 (b, 4H, Pt—O(CH$_2$CH$_2$)$_2$). $^{13}$C{$^1$H}NMR (125.7 MHz, THF): δ=161 (b, ipso B(C$_6$H$_5$)$_2$), δ=136.3 (s, ortho Pt(C$_6$H$_5$)), δ=135.4 (d, ipso P(C$_6$H$_5$)$_2$, $^1$J$_{P-C}$=43.8 Hz), δ=133.0 (d, ortho P(C$_6$H$_5$)$_2$, $^2$J$_{P-C}$=10.7 Hz), δ=132.9 (d, ortho P(C$_6$H$_5$)$_2$ $^2$J$^{P-C}$=11.2 Hz), δ=132.1 (d, ipso P(C$_6$H$_5$) $^1$J$_{P-C}$=57.7 Hz), δ=131.5 (s, ortho B($C_6H_5$), δ=129.2 (s, meta P(($C_6H_5$)$_2$), δ=129.1 (s, meta P($C_6H_5$)$_2$), δ=127.6 (d, para P($C_6H_5$)$_2$, $^4J_{P-C}$=9.1 Hz), δ=126.9 (d, para P($C_6H_5$)$_2$, $^4J_{P-C}$=11.2 Hz), δ=126.4 (d, meta Pt($C_6H_5$), $^4J_{P-C}$=9.6 Hz), δ=125.5 (s, meta B($C_6H_5$)$_2$), δ=122.6 (s, para Pt($C_6H_5$)), δ=121.2 (s, para B($C_6H_5$)$_2$), δ=67 (Pt—O($\underline{C}H_2CH_2$)$_2$), δ=26 (Pt—O($CH_2\underline{C}H_2$)$_2$), δ=21 (b,[Ph$_2$B($\underline{C}H_2$PPh$_2$)$_2$]), δ=17 (b, [Ph$_2$B($\underline{C}H_2$PPh$_2$)$_2$]). $^{31}$P{$^1$H}NMR (121.4 MHZ, THF): δ=28.60 ($^1J_{Pt-P}$=1740 Hz, $^2J_{P-P}$=23 Hz), δ=11.20 ($^1J_{Pt-P}$=4393 Hz, $^2J_{P-P}$=23 Hz). $^{11}$B{$^1$H}NMR (128.3 MHz, THF): δ=−14.9.

Reaction of (4) With Benzene

Solid 4 was generated as above and dissolved in benzene (2 mL). The solution was concentrated in vacuo (vol≈0.5 mL). Benzene was added (1 mL), and the solution was again concentrated in vacuo (vol≈0.7 mL). Concentration of the benzene solution serves to ensure complete removal of residual pentane. The solution was placed in an NMR tube, and an initial $^{31}$P NMR spectrum showed the presence of one species (4). The NMR tube was heated to 50° C. and monitored by $^{31}$P NMR spectroscopy. After 4 h, $^{31}$P NMR spectroscopy showed the presence of 4 products, where (5) was the major product (ca.80%). The identities of the three minor byproducts have yet to be confirmed. They may result from (i)ligand activation, (ii)THF activation, or (iii) bimolecular reaction pathways.

Analogous to its reactivity with benzene, (4) was found to react with toluene preferentially at the C—H bonds of the aryl ring. There is no evidence for competitive benzylic C—H activation. Spectroscopic evidence suggests that the predominant isomer formed is the p-tolyl platinum complex and we the product ratio of 3:1:1 was tentatively assigned to the para:meta:ortho isomers, respectively.

EXAMPLE 5

Bond Activation Activity of (4)

Preliminary studies have been conducted to evaluate the potential of (4) to activate alkyl C—H bonds. As yet, no conclusive observations have been made as to the occurrence of such a reaction. Incubation of a THF solution of (4) under an atmosphere of $^{13}$CH$_4$ at 75° C. for 10 h afforded no detectable incorporation ($^{13}$C NMR) of an isotopically enriched methyl group. This contrasts results reported for complexes with amine and imine donor ligands, where $^{13}$CH$_4$ has been demonstrated to reversibly react with the compounds [(TMEDA)Pt(CH$_3$)(NC$_5$F$_5$)]$^+$ in pentafluoropyridine and [(ArNdC-CdNAr)Pt(CH$_3$)(H$_2$O)]$^−$ in DCM. Additionally, no reaction occurred upon dissolution of (4) in a 1:1 THF:cyclohexane mixture at 75° C. over a period of 12 h. A possible reaction between (4) and the C—H bonds of methane or cyclohexane is likely inhibited by the presence of a large excess of tetrahydrofuran. Complex (4), while soluble in aromatic hydrocarbons, reacts rapidly with them relative to other, nonaromatic solvent molecules; however, (4) is not appreciably soluble in simpler hydrocarbons such as pentane and cyclohexane, and hence its reactivity in the absence of solubilizing THF equivalents has yet to be determined.

EXAMPLE 6

Synthesis of (CH$_3$)$_2$N(BH$_3$)CH$_2$Li.(THF) (6)

The room temperature addition of n-BuLi to a THF solution of Me$_3$N.BH$_3$ cleanly affords (CH$_3$)$_2$N(BH$_3$)CH$_2$Li (THF) (6) as a white, microcrystalline solid. Details of the reaction are as follows.

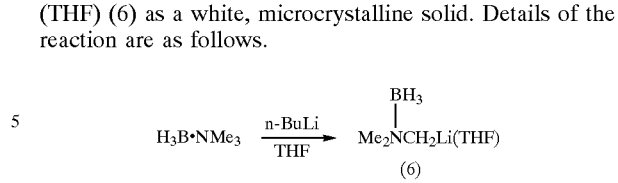

A solution of 1.6 M n-BuLi in hexanes (85.7 ml, 0.137 mol) was added portion-wise to a stirring solution of H$_3$B.NMe$_3$ (10 g, 0.137 mol) dissolved in THF (20 mL) under a dinitrogen atmosphere. Addition was complete after 5 min. Concentration of the reaction solution to 50 mL after stirring for 5 h resulted in precipitation of (6). The reaction solution was decanted from the product, which was washed with petroleum ether (3×40 mL), and dried in vacuo affording spectroscopically pure (6), (9.2 g, 44%). The mother liquor was further concentrated to yield a second crop of (6) (3.2 g). The total isolated yield was 12.4 g (60 %).

$^1$H NMR (C$_6$D$_6$, 300 MHz, 25° C.): δ3.55 (m, 4H, (CH$_2$C$\underline{H}_2$)$_2$O—Li), 2.68 (s, 6H, (Li—CH$_2$N(C$\underline{H}_3$)$_2$)), 2.01 (bs, 2H, (Li—C$\underline{H}_2$N(CH$_3$)$_2$)), 1.30 (m, 4H, (C$\underline{H}_2$CH$_2$)$_2$O—Li). $^{13}$C NMR (C$_6$D$_6$, 75.409 MHz, 25° C.): δ69 (Li—$\underline{C}$H$_2$N(CH$_3$)$_2$, 67 (($\underline{C}$H$_2$CH$_2$)$_2$O—Li), 60.2 (Li—CH$_2$N($\underline{C}$H$_3$)$_2$), 26 (( CH$_2$$\underline{C}$H$_2$)$_2$O—Li). $^{11}$B{$^1$H}NMR (C$_6$D$_6$, 128.3 MHz, 25° C.): δ−10.16

EXAMPLE 7

Synthesis of [Ph$_2$B(CH$_2$N(BH$_3$)(CH$_3$)$_2$)$_2$][Li(TMEDA)$_2$] (7)

Addition of (CH$_3$)$_2$N(BH$_3$)CH$_2$Li(THF) (6) to half an equivalent of Ph$_2$BCl (25° C.; toluene) generates the borane-protected amino(borate) complex [Ph$_2$B(CH$_2$N(BH$_3$)Me$_2$)$_2$][Li]. This species is conveniently precipitated from Et$_2$O by addition of TMEDA to produce [Ph$_2$B(CH$_2$N(BH$_3$)Me$_2$)$_2$][Li(TMEDA)$_2$] (7) as a white solid. Details of the reaction follows.

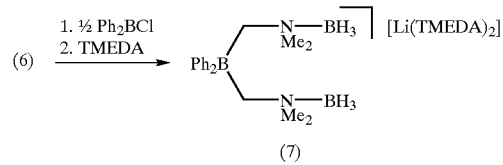

A solution of Ph$_2$BCl (268 mg, 1.3 mmol) in toluene (5 mL) was added dropwise to (CH$_3$)$_2$N(BH$_3$)CH$_2$Li.(THF) (6) (405 mg, 2.6 mmol) in toluene (6 mL). When the addition was complete after 5 min., the solution became turbid as LiCl precipitated from solution. The reaction was allowed to stir for 6 hours when the toluene was removed in vacuo. The resulting oily solid was taken up in 5 mL Et$_2$O and filtered through Celite to remove the LiCl salts. Upon the addition of TMEDA (350 mg, 3 mmol), (7) precipitated from the ether solution. (7) was isolated via filtration and washed with petroleum ether (3×10 mL), and dried in vacuo affording spectroscopically pure (7), (510 mg, 69%). Crystals were grown via petroleum ether diffusion into a benzene solution.

$^1$H NMR (C$_6$D$_6$, 300 MHz, 25° C.): δ8.18 (d, J=7.2 Hz, 4H, ortho B(C$_6$$\underline{H}_5$)$_2$), 7.44 (t, J=7.2 Hz, 4H, meta B(C$_6$$\underline{H}_5$)$_2$), 7.26 (t, J=7.2 Hz, 2H, para B(C$_6$$\underline{H}_5$)$_2$), 3.27 (b, 4H, Ph$_2$B(C$\underline{H}_2$N(BH$_3$)(CH$_3$)$_2$), 2.33 (s, 12H, Ph$_2$B(CH$_2$N(BH$_3$)(C$\underline{H}_3$)$_2$)), 1.954 (s, 34H, TMEDA-Li). $^{13}$C NMR (C$_6$D$_6$, 75.409 MHz, 25° C.): δ162 (b, ipso (B($\underline{C}_6$H$_5$)$_2$), 136 (s, ortho (B(C̲₆H₅)₂), 127.6 (s, meta (B(C̲₆H₅)₂), 124.4 (s, para (B(C̲₆H₅)₂), 72 (b, Ph₂B(C̲H₂N(BH₃)(CH₃)₂), 58 (s, (C̲H₃)₂N(CH₂)₂), 53 (s, (CH₃)₂N̲(C̲H₂)₂), 47 (s, Ph₂B(CH₂N(BH₃)(C̲H₃)₂). ¹¹B{¹H}NMR (C₆D₆, 128.3 MHz, 25° C.): δ−7.77 Ph₂B(CH₂N(B̲H₃)(CH₃)₂), −13.9 Ph₂B̲(CH₂N(BH₃)(CH₃)₂). ES-MS (Electrospray): calculated for C₁₈H₃₂B₃N₂ (M)⁻ m/z 309, found (M+H)⁻ m/z 309, 295 (M−BH₃). Anal. Calculated for C₃₀H₆₄B₃LiN₆: C, 65.72; H, 11.77; N, 15.33. Found: C, 65.38; H, 11.69, N, 15.08.

EXAMPLE 8

Synthesis of [Ph₂B(CH₂NMe₂)₂][Li] (8)

To derive the target ligand, numerous methods were evaluated to remove the borane protecting group from [Ph₂B(CH₂N(BH₃)Me₂)₂]⁻. Borane liberation from alkylamines is traditionally accomplished by transfer to another strong Lewis base, acidification, or oxidation (Schmidbaur, *J. Organomet. Chem.* 200:287 (1980); Imamoto et al., *J. Am. Chem. Soc.* 112:5244 (1991); Brunel et al., *Coord. Chem. Rev.* 665:178–180 (1998); Carboni et al., *Tetrahedron* 55:1197 (1999); borane protected benzylic amines and substituted aziridines have been alkylated via intermediate generation of a benzylic or aziridinyl carbanion in Ebden et al, *Tetrahedron* 1998, 54(42):129 (1998) and Vedejs et al.,*J. Am. Chem. Soc.* 119:6941 (1997); and Couturier et al, *Organic Lett.* 3(3):465 (2001)). Unfortunately, [Ph₂B(CH₂N(BH₃)Me₂)2]⁻ degrades to Me₃N.BH₃ on exposure to strong acid (e.g. HCl) and resists borane oxidation in the presence of Pd/C in methanol (25 wt % Pd/C, 3 days, 25° C.). The focus turned to a Lewis base deprotection strategy. The system of choice proved to be a 25-fold excess of DABCO (toluene, 100° C., complete and quantitative after 10 h as determined by ¹¹B NMR). The excess DABCO was effectively recovered by sublimation (120° C., 10 torr), and the target ligand [Ph₂BN^{Me}₂] was isolated as its lithium salt [Ph₂BN^{Me}₂] [Li] (8), in yields typically exceeding 80%. Details of the reaction are as follows.

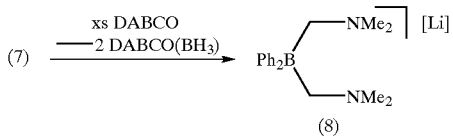

[Ph₂B(CH₂NMe₂(BH₃))₂][Li(TMEDA)₂] (7) (1.0 g, 1.78 mmol) and DABCO (5.0 g, 44.6 mmol) were dissolved in toluene (15 mL). The solution was heated to 100° C. for 10 hours. Borane transfer was monitored by ¹¹B NMR. The toluene was removed in vacuo and the unused DABCO reagent was sublimed under static vacuum from the solid mixture at 60° C. The DABCO.BH₃ complex was sublimed under dynamic vacuum at 125° C. The remaining white solid was washed with pet ether (2×2 mL) and dried in vacuo to yield 442 mg of (8) (86%).

¹H NMR (acetone-d₆, 300 MHz, 25° C.): δ7.31 (d, J=7.2 Hz, 4H, ortho B(C₆H₅)₂), 6.98 (t, J=7.2 Hz, 4H, meta B(C₆H̲₅)₂), 6.80 (t, J=7.2 Hz, 2H, para B(C₆H̲₅)₂), 2.81 (q, ²J_{B-H}=3.6 Hz, 4H, Ph₂B(C̲H₂N(CH₃)₂), 2.47 (s, 12H, Ph₂B(CH₂N(C̲H₃)₂). ¹³C NMR (acetone-d₆, 125.7 MHz, 25° C.): δ162.4 (q, ¹J_{B-C}=50.3 Hz, ipso B(C̲₆H₅)₂), 132.8 (s, ortho B(C̲₆H₅)₂), 127 (s, meta B(C̲₆H₅)₂), 123 (s, para B(C̲₆H₅)₂), 63.1 (q, ¹J_{B-C}=43.4 Hz, Ph₂B(C̲H₂N(CH₃)₂), 47.7 (s, Ph₂B(CH₂N(C̲H₃)₂). ¹¹B{¹H}NMR (acetone-d₆, 128.3 MHz, 25° C.): δ−17.8. ES-MS (Electrospray): calculated for C₁₈H₂₆BN₂ (M)⁻ m/z 281, found (M)⁻ m/z 281; (M+2H)⁺ m/z 283, found 283.

EXAMPLE 9

Synthesis of [Ph₂B(CH₂NMe₂)₂][NEt₄] (9)

The ammonium salt [Ph₂BN^{Me}₂][NEt₄] (9) forms readily upon addition of an ethanolic solution of Et₄NBr to (3). Details of the reaction are as follows.

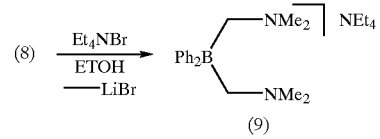

Alternately, KOC(CH₃)₃ (55 mg, 0.5 mmol) in 0.5 mL THF was added dropwise to [Ph₂B(CH₂NMe₂)₂][H] (100 mg, 0.25 mmol) in benzene (2 mL). [Ph₂B(CH₂NMe₂)₂][K] precipitated from solution as a white solid. The solution was decanted and the solids dried and isolated. The solids were washed with benzene (3×3 mL) and petroleum ether (3×1.5 mL) and dried in vacuo. Solid [Ph₂B(CH₂NMe₂)₂][K] (25 mg, 0.078 mmol) was dissolved in EtOH (1.5 mL) and added to a solution of [NEt₄][Br] (19.7 mg, 0.094 mmol) in EtOH (1 mL). Solid KBr precipitates from solution and was filtered over a sintered glass frit. The EtOH was removed in vacuo producing a white solid. The solids were washed with EtOH/petroleum ether (1:3, 3 mL) to yield (9) (29.6 mg, 92%).

¹H NMR (acetone-d₆, 300 MHz, 25° C.): δ7.33 (d, J=7.5 Hz, 4H, ortho B(C₆H₅)₂), 6.92 (t, J=7.5 Hz, 4H, meta B(C₆H̲₅)₂), 6.73 (t, J=7.5 Hz, 2H, para B(C₆H̲₅)₂), 3.42 (q, J=7.2 Hz, 8H, N(C̲H₂CH₃)₄), 2.57 (m, 4H, Ph₂B(C̲H₂N(CH₃)₂), 2.22 (s, 12H, Ph₂B(CH₂N(C̲H₃)₂), 3.42 (tt, J=2.1, 7.2 Hz, 12H, N(CH₂C̲H₃)₄). ¹³C NMR (acetone-d₆, 125.7 MHz, 25° C.): δ162.4 (q, ¹J_{B-C}=50.3 Hz, ipso B(C̲₆H₅)₂), 132.8 (s, ortho B(C̲₆H₅)₂), 127 (s, meta B(C̲₆H₅)₂), 123 (s, para B(C̲₆H₅)₂), 63.1 (q, ¹J_{B-C}=43.4 Hz, Ph₂B(C̲H₂N(CH₃)₂), 47.7 (s, Ph₂B(CH₂N(C̲H₃)₂). ¹¹B{¹H}NMR (acetone-d₆, 128.3 MHz, 25° C.): δ−18.0. ES-MS (Electrospray): calculated for C₁₈H₂₆BN₂ (M)⁻ m/z 281, found (M)⁻ m/z 281; (M+2H)⁺ m/z 283, found 283.

EXAMPLE 10

Synthesis of [Ph₂B(CH₂N(BH₃)(CH₃)₂)₂][NEt₄] (10)

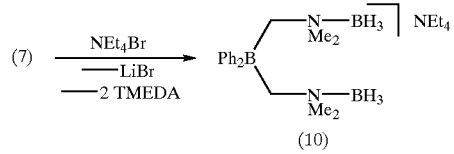

NEt₄Br (21 mg, 0.1 mmol) in EtOH (0.5 mL) was added to a solution of [Ph₂B(CH₂N(BH₃)(CH₃)₂)₂][Li(TMEDA)₂] (7) (218 mg, 0.091 mmol) in 1 mL of EtOH. Crystals of (10) grew from the solution. The remaining solution was decanted and the crystals washed with EtOH (2×1 mL) and pet ether (2×1 mL). The solids were dried in vacuo to yield 154.7 mg (88.6%).

¹H NMR (acetone-d₆, 300 MHz, 25° C.): δ7.64 (d, J=7.5 Hz, 4H, ortho B(C₆H₅)₂), 7.08 (t, J=7.5 Hz, 4H, meta B(C₆H̲₅)₂), 6.92 (t, J=7.5 Hz, 2H, para B(C₆H̲₅)₂), 3.46 (q, J=7.2 Hz, 8H, N(C̲H₂CH₃)₄), 2.78 (q, ²J_{B-H}=3.6 Hz, 4H, Ph₂B(C̲H₂N(BH₃)(CH₃)₂)), 1.96 (s, 12H, Ph₂B(CH₂N(BH₃)(C H$_3$)$_2$)), 1.38 (tt, J=2.1, 7.2 Hz, 12 H, N(CH$_2$CH$_3$)$_4$). $^{13}$C NMR (acetone-d$_6$, 125.7 MHz, 25° C): δ158 (q, ipso B(C$_6$H$_5$)$_2$), 136 (s, ortho B(C$_6$H$_5$)$_2$), 127 (s, meta B(C$_6$H$_5$)$_2$), 124 (s, para B(C$_6$H$_5$)$_2$), 69.8 (q, $^1J_{B-C}$=43.2 Hz, Ph$_2$B(CH$_2$N(CH$_3$)$_2$), 47.7 (s, Ph$_2$B(CH$_2$B(CH$_2$N(CH$_3$)$_2$). $^{11}$B{$^1$H}NMR (C$_6$D$_6$, 128.3 MHz, 25° C.): δ–5.1, –14. ES-MS (Electrospray): calculated for C$_{18}$H$_{32}$B$_3$N$_2$ (M)$^-$ m/z 309, found (M+H)$^-$ m/z 309, 295 (M-BH$_3$). Anal. Calculated for C$_{26}$H$_{52}$B$_3$N$_3$; C, 71.11; H, 11.94; N, 9.57. Found: C, 70.98; H, 11.90; N, 9.38.

EXAMPLE 11

Synthesis of [Ph$_2$B(CH$_2$NMe$_2$)$_2$][H] (11)

An attempt to deprotect the ammonium salt [Ph$_2$B(CH$_2$N(BH$_3$)Me$_2$)$_2$][NEt$_4$] (10) resulted in a Hoffmann degradation of the ammonium cation and led to the formation of [Ph$_2$BNMe$_2$][H] (11). The fortuitous formation of this free acid derivative provides access to a range of other salts, [Ph$_2$BN$^{Me}$$_2$][M$^+$], by simple base deprotonation (where M$^+$=Li, Na, K from $^n$BuLi, NaO$^t$Bu, and KO$^t$Bu, respectively). Details of the reaction are as follows.

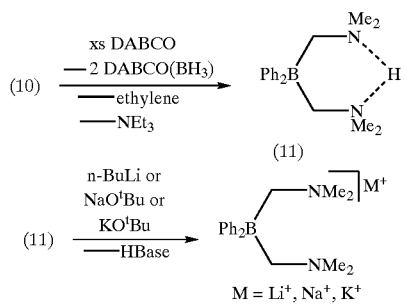

[Ph$_2$B(CH$_2$NMe$_2$(BH$_3$))$_2$][NEt$_4$] (10) (261 mg, 0.06 mmol) and DABCO (3.33 g, 0.03 mol) were suspended in toluene (5 mL). The solution was heated to 100° C. for 10 hours. Borane transfer was monitored by $^{11}$B NMR. The toluene was removed in vacuo and the unused DABCO reagent was sublimed under vacuum from the solid mixture at 60° C. Upon dissolving the solids in EtOH, a white precipitate formed. The EtOH was decanted from the solid. The solid was washed with petroleum ether (2×2 mL) and dried in vacuo to yield 78 mg of (11) (47%).

$^1$H NMR (acetone-d$_6$, 300 MHz, 25° C.): δ7.31 (d, J=7.2 Hz, 4H, ortho B(C$_6$H$_5$)$_2$), 6.98 (t, J=7.2 Hz, 4H, meta B(C$_6$H$_5$)$_2$), 6.80 (t, J=7.2 Hz, 2H, para B(C$_6$H$_5$)$_2$), 2.81 (q, $^2J_{B-H}$=3.6 Hz, 4H, Ph$_2$B(CH$_2$N(CH$_3$)$_2$), 2.47 (s, 12H, Ph$_2$B(CH$_2$N(CH$_3$)$_2$). $^{11}$B{$^1$H}NMR (acetone-d$_6$, 128.3 MHz, 25° C.): δ–24. ES-MS (Electrospray): calculated for C$_{18}$H$_{26}$BN$_2$ (M)$^-$ m/z 281, found (M)$^-$ m/z 281; (M+2H)$^+$ m/z 283, found 283.

EXAMPLE 12

Synthesis of Ph$_2$B(CH$_2$NMe$_2$)$_2$Rh(NBD) (12)

The lithium salt [Ph$_2$BN$^{Me}$$_2$][Li] (8) underwent smooth transmetallation with [(NBD)RhCl]$_2$ to afford a yellow, crystalline rhodium complex {Ph$_2$B(CH$_2$NMe$_2$)$_2$}Rh(NBD) (12). Details of the reaction are as follows.

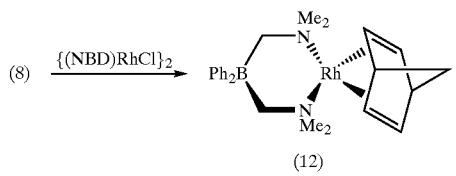

A solution of [Ph$_2$B(CH$_2$NMe$_2$)$_2$][Li] (8) (50.2 mg, 0.174 mmol) in acetone (2 mL) was added to a solution of [(NBD)RhCl]$_2$ (40.2 mg, 0.173 mmol) in benzene (1 mL) at room temperature. After stirring for 2 h, the solvent was removed in vacuo. The yellow solid was dissolved in benzene and filtered through a Celite plug to yield a yellow solution. The benzene was removed in vacuo, then the solids were washed with petroleum ether (3×1.5 mL). The solids were dried in vacuo to yield 71.4 mg (86%) of (12).

$^1$H NMR (C$_6$D$_6$, 300 MHz, 25° C.): δ7.66 (m, 4H, ortho B(C$_6$H$_5$)$_2$), 7.37 (t, J=7.2 Hz, 4H, meta B(C$_6$H$_5$)$_2$), 7.15 (t, J=7.2 Hz, 2H, para B(C$_6$H$_5$)$_2$), 3.089 (b, 2H, NBD), 2.91 (dd, J=2.1, 5.1 Hz, 4H, NBD), 2.62 (q, $^2J_{B-H}$=3.6 Hz, 4H, Ph$_2$B(CH$_2$N(CH$_3$)$_2$), 1.66 (s, 12H, Ph$_2$B(CH$_2$N(CH$_3$)$_2$), 0.84 (b, 2H, NBD). $^{13}$C NMR (C$_6$D$_6$, 125.7 MHz, 25° C.): δ165 (m, ipso B(C$_6$H$_5$)$_2$), 132.6 (s, ortho B(C$_6$H$_5$)$_2$), 127.6 (s, meta B(C$_6$H$_5$)$_2$), 123.5 (s, para B(C$_6$H$_5$)$_2$), 65.2 (q, $^1J_{B-C}$=44.3 Hz, Ph$_2$B(CH$_2$N(CH$_3$)$_2$), 62.7 (NBD), 57.7 (d, $^1J_{Rh-C}$=10 Hz, NBD), 52.7 (s, Ph$_2$B(CH$_2$N(CH$_3$)$_2$), 50.1 (NBD). $^{11}$B{$^1$H}NMR (acetone-d$_6$, 128.3 MHz, 25° C.): δ–17.5 EM-MS (Electrospray): calculated for C$_{25}$H$_{34}$BN$_2$Rh (M)$^-$ m/z 476, found (M)$^+$ m/z 476. Anal. Calculated for C$_{25}$H$_{34}$BN$_2$Rh: C, 63.05; H, 7.20; N, 5.88. Found: C, 62.85; H, 7.18; N, 5.53.

EXAMPLE 13

Synthesis of Ph$_2$B(CH$_2$NMe$_2$)$_2$Rh(NCCH$_3$)$_2$ (13)

Hydrogenation of (12) in acetonitrile afforded the well-behaved catalyst precursor {Ph$_2$BN$^{Me}$$_2$}Rh(NCCH$_3$)$_2$ (13). Details of the reaction are as follows.

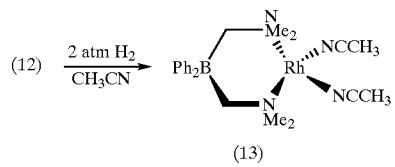

A solution of Ph$_2$B(CH$_2$NMe$_2$)$_2$Rh(NBD) (12) (25 mg, 0.054 mmol) in THF/acetonitrile (1:1, 1.5 mL) was charged to a Fisher-Porter bottle under 40 psi of hydrogen. After stirring vigorously for 1 hr, yellow precipitate was apparent. The remaining solvent was removed in vacuo to produce a yellow solid (13). The solids were washed with petroleum ether and dried in vacuo (23 mg, 92%).

$^1$H NMR (C$_6$D$_6$, 300 MHz, 25° C.): δ7.67 (m, 4H, ortho B(C$_6$H$_5$)$_2$), 7.39 (t, J=7.2 Hz, 4H, meta B(C$_6$H$_5$)$_2$), 7.16 (t, J=7.2 Hz, 2H, para B(C$_6$H$_5$)$_2$), 2.70 (q, $^2J_{B-H}$=3.6 Hz, 4H, Ph$_2$B(CH$_2$N(CH$_3$)$_2$), 1.71 (s, 12H, Ph$_2$B(CH$_2$N(CH$_3$)$_2$), 1.37 (s, 6H, (NCCH$_3$)). $^{13}$C NMR (C$_6$D$_6$, 125.7 MHz, 25° C.): δ165 (m, ipso B(C$_6$H$_5$)$_2$), 132.6 (s, ortho B(C$_6$H$_5$)$_2$), 127.6 (s, meta B(C$_6$H$_5$)$_2$), 123.5 (s, para B(C$_6$H$_5$)$_2$), 65.2 (q, $^1J_{B-C}$=44.3 Hz, Ph$_2$B(CH$_2$N(CH$_3$)$_2$), 52.7 (s, Ph$_2$B(CH$_2$N(CH$_3$)$_2$). $^{11}$B{$^1$H}NMR (C$_6$D$_6$, 128.3 MHz, 25° C.): δ–17.5. ES—MS (Electrospray): calculated for C$_{25}$H$_{34}$BN$_2$Rh (M)$^-$ m/z 466, found (M)$^+$ m/z 425 (M-NCCH$_3$), 304 (M-2NCCH$_3$).

EXAMPLE 14

Synthesis of Ph$_2$B(CH$_2$NMe$_2$)$_2$Rh(CO)$_2$ (14)

Notably, acetonitrile adducts of more typical, cationic rhodium precursors, [L$_2$Rh(NCCH$_3$)$_2$]$^+$, typically show poor catalytic activity because acetonitrile binds the cationic center too tightly. It is theorized that the zwitterionic {Ph$_2$BNMe$_2$}Rh(NCCH$_3$)$_2$ complex is a good pre-catalyst due to its attenuated electrophilicity by comparison to traditional, truly cationic systems. To qualitatively examine the validity of this argument, {Ph$_2$B(CH$_2$NMe$_2$)$_2$}Rh(CO)$_2$ (14) was prepared and its i)(CO) stretching vibrations compared with the cationic, structural analog [(TMEDA)Rh(CO)$_2$][ClO$_4$] (Uson et al., *J. Organomet. Chem.* 105(3):365 (1976)). The zwitterionic (14) was found to be more electron rich ((14), υ(CO)(CH$_2$Cl$_2$): 2069, 1992 cm$^{-1}$; [(TMEDA)Rh(CO)$_2$][ClO$_4$] υ(CO) (CH$_2$Cl$_2$): 2080, 2010 cm$^{-1}$. Details of the reaction are as follows.

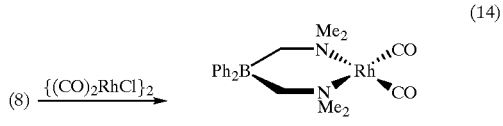

Alternately, a solution of [(CO)$_2$RhCl]$_2$ (5 mg, 0.013 mmol) in THF (0.5 mL) was added to a stirring solution of [Ph$_2$B(CH$_2$NMe$_2$)$_2$][NEt$_4$] (9) (10.6 mg, 0.013 mmol) in THF (1 mL) at room temperature. After stirring for 5 minutes, the solution was filtered through a Celite plug and then the THF was removed in vacuo to yield (14).

$^1$H NMR (C$_6$D$_6$, 300 MHz, 25° C.): δ7.66 (m, 4H, ortho B(C$_6$H$_5$)$_2$), 7.37 (t, J=7.2 Hz, 4H, meta B(C$_6$H$_5$)$_2$), 7.15 (t, J=7.2 Hz, 2H, para B(C$_6$H$_5$)$_2$), 2.66 (q, $^2$J$_{B-H}$=3.6 Hz, 4H, Ph$_2$B(CH$_2$N(CH$_3$)$_2$), 1.73 (s, 12H, Ph$_2$B(CH$_2$N(CH$_3$)$_2$). $^{13}$C NMR (C$_6$D$_6$, 125.7 MHz, 25° C.): δ165 (m, ipso B(C$_6$H$_5$)$_2$), 132.6 (s, ortho B(C$_6$H$_5$)$_2$), 127.6 (s, meta B(C$_6$H$_5$)$_2$), 123.5 (s, para B(C$_6$H$_5$)$_2$), 65.2 (q, $^1$J$_{B-C}$=44.3 Hz, Ph$_2$B(CH$_2$N(CH$_3$)$_2$), 52.7 (s, Ph$_2$B(CH$_2$N(CH$_3$)$_2$). $^{11}$B{$^1$H} NMR (C$_6$D$_6$, 128.3 MHz, 25° C.): δ−17.3. IR: (CH$_2$Cl$_2$) v$_{CO}$= 2069.6, 1992 cm$^{-1}$.

EXAMPLE 15

Catalysis Reactions with (13)

It is well known that cationic rhodium(I) precursors supported by neutral, bidentate ligands can be excellent catalysts for organometallic transformations. These processes include catalytic hydrogenation (Schrock et al., *J. Am. Chem. Soc.* 93:3091 (1971); Crabtree, *Acc. Chem. Res.* 12:331 (1979); and Crabtree, Homogeneous Catalysis (Ch. 9). *The Organometallic Chemistry of the Transition Metals.* 3$^{rd}$ Edition; John Wiley & Sons: New York, N.Y., 206–236 (2001)), hydrosilation (Ojima, *The Chemistry of Organic Silicon Compounds*; Patai, S.; Rappoport, Z., Eds.; Wiley: New York, 1989; Chapter 25), hydroboration (Burgess et al., *Chem. Rev.* 91:1179 (1991); and Evans et al., *J. Am. Chem. Soc.* 110:6917 (1988)), hydroamination (Burling et al., *Organometallics* 19:87 (2000); and Hartung et al., *J. Org. Chem.* 66:6339 (2001)), and hydroacylation reactions (Bosnich, *Acc. Chem. Res.* 31:667 (1998)). The mediation of related transformations by the neutral, but formally zwitterionic "{Ph$_2$BN$^{Me}$$_2$} Rh$^+$" precursors was evaluated. Details of the reaction are as follows.

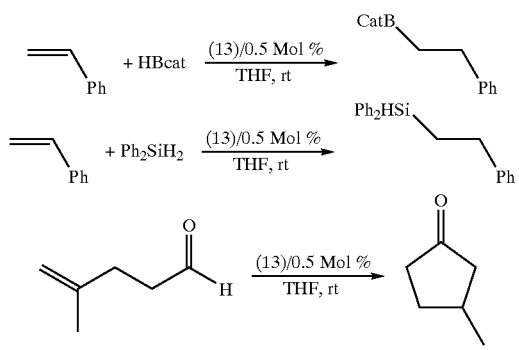

Styrene (44.5 mg, 0.43 mmol) and catecholborane (46 mg, 0.38 mmol) were added to a THF (1 mL) solution of (13) (1 mg, 2 μmol). The reaction was monitored by $^{11}$B NMR and borane transfer was judged complete at 1.5 h. GC/MS analysis showed the product peaks at m/z=224, 104. Compound (13) was shown to be an active catalyst for this hydroboration reaction (93% GC/MS, 0.5 mol % of (13), 1.5 h)

Styrene (44.5 mg, 0.43 mmol) and diphenylsilane (70 mg, 0.38 mmol) were added to a C$_6$D$_6$ (0.7 mL) solution of (13) (1 mg, 2 μmol). The reaction was monitored by $^1$H NMR and silane transfer was judged complete at 1 h. GC/MS analysis showed the product peaks at m/z=288, 104. Compound (13) was shown to be an active catalyst for this hydrosilation reaction (96% GC/MS, 0.5 mol % of (13), 1 h)

4-methyl-4-pentenal (42 mg, 0.43 mmol) was added to a C$_6$D$_6$ (0.7 mL) solution of (13) (1 mg, 2 μmol) in an NMR tube. The reaction was monitored by $^1$H NMR and conversion to cyclopentanone was judged complete after 1 h (compared to an authentic sample). Compound (13) was shown to be a very active catalyst for the intramolecular hydroacylation of 4-methyl-4-pentenal to 3-methylcyclopentanone (95% $^1$H NMR, 0.5 mol % of (13), 1 h).

All patents, publications, and other published documents mentioned or referred to in this specification are herein incorporated by reference in their entirety.

It is to be understood that while the invention has been described in conjunction with the preferred specific embodiments hereof, the foregoing description, as well as the examples which are intended to illustrate and not limit the scope of the invention, it should be understood by those skilled in the art that various changes may be made and equivalents may be substituted without departing from the scope of the invention. Other aspects, advantages and modifications will be apparent to those skilled in the art to which the invention pertains.

Accordingly, the scope of the invention should therefore be determined with reference to the appended claims, along with the full range of equivalents to which those claims are entitled.

We claim:
1. An anionic borate ligand having the formula:

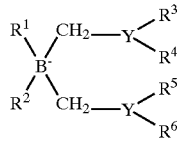

wherein:
R$^1$ and R$^2$ are independently selected from the group consisting of alkyl and aryl;
Y is P; and
R$^3$, R$^4$, R$^5$ and R$^6$ are independently selected from the group consisting of alkyl and aryl.

2. The ligand of claim 1 wherein R$^1$ and R$^2$ are phenyl and R$^3$, R$^4$, R$^5$ and R$^6$ are phenyl.

3. The ligand of claim 1 wherein R$^1$ and R$^2$ are 3-methylphenyl and R$^3$, R$^4$, R$^5$ and R$^6$ are phenyl.

4. The ligand of claim 1 wherein R$^1$ and R$^2$ are 3-t-butylphenyl and R$^3$, R$^4$, R$^5$ and R$^6$ are phenyl.

5. The ligand of claim 1 wherein R$^1$ and R$^2$ are 3-methoxyphenyl and R$^3$, R$^4$, R$^5$ and R$^6$ are phenyl.

6. The ligand of claim 1 wherein R$^1$ and R$^2$ are 2,4-di(trifluoromethyl)phenyl and R$^3$, R$^4$, R$^5$ and R$^6$ are phenyl.

7. The ligand of claim 1 wherein R$^1$ and R$^2$ are 1,2,3,4,5-pentafluorophenyl and R$^3$, R$^4$, R$^5$ and R$^6$ are phenyl.

8. The ligand of claim 1 wherein R$^1$ and R$^2$ are phenyl-d$_5$ and R$^3$, R$^4$, R$^5$ and R$^6$ are phenyl.

9. The ligand of claim 1 wherein R$^1$ and R$^2$ are phenyl and R$^3$, R$^4$, R$^5$ and R$^6$ are t-butyl.

10. The ligand of claim 1 wherein R$^1$ and R$^2$ are is 3-t-butylphenyl and R$^3$, R$^4$, R$^5$ and R$^6$ are t-butyl.

11. The ligand of claim 1 wherein R$^1$ and R$^2$ are is phenyl and R$^3$, R$^4$, R$^5$ and R$^6$ are methyl.

12. The ligand of claim 1 wherein R$^1$ and R$^2$ are is phenyl and R$^3$, R$^4$, R$^5$ and R$^6$ are 3-t-butylphenyl.

13. The ligand of claim 1 wherein R$^1$ and R$^2$ are is phenyl and R$^3$, R$^4$, R$^5$ and R$^6$ are 2,4-di(trifluoromethyl)phenyl.

* * * * *